United States Patent
Bonastre et al.

(10) Patent No.: US 10,016,470 B2
(45) Date of Patent: Jul. 10, 2018

(54) ONCOLYTIC ADENOVIRUSES FOR CANCER TREATMENT

(71) Applicant: DNATRIX, INC., Houston, TX (US)

(72) Inventors: Ramon Alemany Bonastre, Barcelona (ES); Juan Jose Rojas Exposito, Barcelona (ES); Manel Maria Cascallo Piqueras, Barcelona (ES)

(73) Assignee: DNATRIX, INC., Houston, TX (US)

( * ) Notice: Subject to any disclaimer, the term of this patent is extended or adjusted under 35 U.S.C. 154(b) by 0 days.

(21) Appl. No.: 15/144,637

(22) Filed: May 2, 2016

(65) Prior Publication Data

US 2016/0354420 A1  Dec. 8, 2016

Related U.S. Application Data

(63) Continuation of application No. 14/327,840, filed on Jul. 10, 2014, which is a continuation of application No. 12/184,881, filed on Aug. 1, 2008, which is a continuation of application No. PCT/ES2007/000050, filed on Jan. 31, 2007.

(30) Foreign Application Priority Data

Feb. 1, 2006 (ES) .................... 200600216

(51) Int. Cl.
| | |
|---|---|
| *A61K 35/761* | (2015.01) |
| *C12N 7/01* | (2006.01) |
| *C12N 15/861* | (2006.01) |
| *C12N 15/11* | (2006.01) |
| *C12N 15/34* | (2006.01) |
| *C12N 7/00* | (2006.01) |
| *C12N 15/86* | (2006.01) |

(52) U.S. Cl.
CPC ............ *A61K 35/761* (2013.01); *C12N 7/00* (2013.01); *C12N 15/86* (2013.01); *C12N 2710/10021* (2013.01); *C12N 2710/10032* (2013.01); *C12N 2710/10043* (2013.01); *C12N 2710/10321* (2013.01); *C12N 2710/10332* (2013.01); *C12N 2710/10343* (2013.01); *C12N 2820/007* (2013.01)

(58) Field of Classification Search
None
See application file for complete search history.

(56) References Cited

U.S. PATENT DOCUMENTS

2006/0147420 A1* 7/2006 Fueyo .................. A61K 48/005
424/93.2
2007/0292396 A1* 12/2007 Fueyo .................. A61K 45/06
424/93.6

FOREIGN PATENT DOCUMENTS

WO    WO 01/49868    * 12/2001

OTHER PUBLICATIONS

Filippova et al, CTCF-binding sites flank CTG/CAG repeats and form a methylation-sensitive insulator at the DM1 locis, Nature Genetics, 2001, pp. 335-343.*
Cheng et al, A Novel TARP-Promoter-Based Adenovirus against Hormone-Dependent and Hormone-Refractory Prostate Cancer, Molecular Therapy vol. 10, No. 2, Aug. 2004, pp. 355-364.*
Steinwaerder and Lieber, Insulation from viral transcriptional regulatory elements improves inducible transgene expression from adenovirus vectors in vitro and in vivo, Gene Therapy (2000) 7, 556-567.*
Majem, M. et al., Control of E1A under an E2F-1 promoter insulated with the myotonic dystrophy locus insulator reduces the toxicity of oncolytic adenovirus Ad-D24RGD, Cancer Gene Therapy (2006) 13, 696-705, Nature Publishing Group.

* cited by examiner

*Primary Examiner* — Maria Marvich
(74) *Attorney, Agent, or Firm* — Reed Smith LLP; Robert R. Riddle; Matthew S. Gibson

(57) ABSTRACT

The invention relates to an oncolytic adenovirus for the treatment of cancer, containing a human DNA sequence isolating a promoter conferring selective expression on an adenoviral gene. Said adenovirus can also contain a sequence that optimizes the protein translation of an adenoviral gene regulated by a promoter conferring tumor selectivity. The invention is suitable for use in the treatment of cancer.

Figure 1:
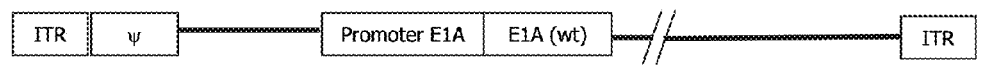
Figure 1:
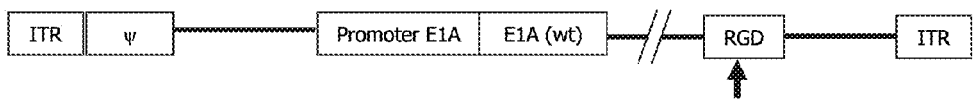
Figure 1:
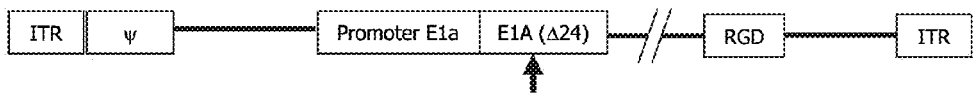
Figure 1:
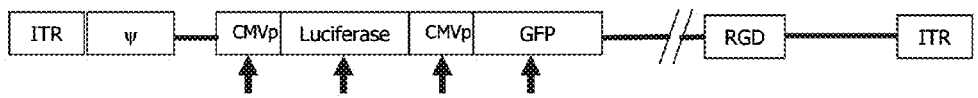
Figure 1:
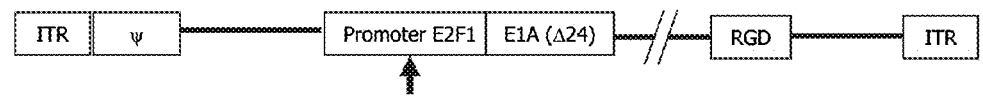
Figure 1:
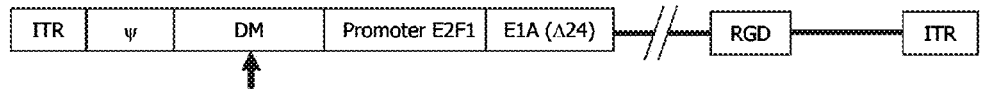
Figure 1:
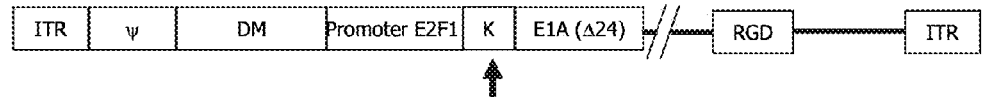

12 Claims, 10 Drawing Sheets
(5 of 10 Drawing Sheet(s) Filed in Color)

AdwtRGD

Ad-Δ24RGD

Ad-TLRGD

ICOVIR1

ICOVIR2

ICOVIR5

ICOVIR7

Normal Cell

Tumor Cell

SKMel-28

— AdwtRGD
---- ICOVIR-2
······ ICOVIR-5

FaDu

ONCOLYTIC ADENOVIRUSES FOR CANCER TREATMENT

CROSS-REFERENCE TO RELATED APPLICATIONS

This application is a continuation of U.S. patent application Ser. No. 14/327,840, filed Jul. 10, 2014, now abandoned, which is a continuation of U.S. patent application Ser. No. 12/184,881, filed Aug. 1, 2008, now abandoned, which is a continuation of International Application No. PCT/ES/2007/000050, filed, Jan. 31, 2007, which claims the benefit of ES Application P200600216, filed Feb. 1, 2006, all of which are incorporated by reference.

SEQUENCE LISTING

This disclosure includes a sequence listing submitted as a text file pursuant to 37 C.F.R. § 1.52(e)(v) named 13-21003-US-C (363849.00015)_SL.txt, created on Nov. 24, 2014, with a size of 9,257 bytes, which is incorporated herein by reference. The attached sequence descriptions and Sequence Listing comply with the rules governing nucleotide and/or amino acid sequence disclosures in patent applications as set forth in 37 C.F.R. § § 1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (No. 2):345-373 (1984). The symbols and format used for nucleotide and amino acid sequence data comply with the rules set forth in 37 C.F.R. § 1.822.

BACKGROUND

The field of the invention is related in general terms to the field of tumor biology. In particular, the invention refers to selective-replication adenoviruses in tumors, known as oncolytic adenoviruses, and their use to inhibit cancer.

The current treatment of cancer is based principally on chemotherapy, radiotherapy, and surgery. Despite a high cure rate of cancer in early stages, the majority of advanced cases of cancer are incurable because they cannot be removed surgically or because the doses administered of radiotherapy or chemotherapy are limited because of their toxicity for normal cells. To alleviate this situation, biotechnological strategies have been developed that seek to increase the potency and selectivity of cancer treatments. Among these, gene therapy and virotherapy use viruses with the aim of treating cancer. In gene therapy, the virus is modified to prevent its replication and to act as a vehicle or vector of the therapeutic genetic material. On the other hand, virotherapy uses viruses that are replicated and propagated selectively in tumor cells[1]. In virotherapy, the tumor cell dies as a result of the cytopathic effect caused by the internal replication of the virus more than because of the effect of a therapeutic gene. Preferential replication in a tumor cell is called oncotropism and the lysis of the tumor is called oncolysis. Viruses that are replicated selectively in tumors are called oncolytic viruses.

Cancer virotherapy significantly predates gene therapy. The first observations of tumor cure with viruses date from early in the last century. Already in 1912, De Pace observed tumor regressions after inoculating the rabies virus in cervical carcinomata[2]. Since then, many types of virus have been injected in tumors to treat them[3]. There are viruses that present a natural oncotropism, for example the autonomous parvovirus, the vesicular-stomatitis virus[5] and the reovirus[6]. Other viruses can be manipulated genetically for selective replication in tumors. For example, the herpes simplex virus (HSV) has been made oncotropic on selecting the gene of ribonucleotide reductase, a dispensable enzyme activity in cells in active proliferation such as tumor cells[7]. However, the adenovirus, in view of its low pathogenicity and high capacity to infect tumor cells, has been the virus used most in both virotherapy and gene therapy for cancer.

The type-5 human adenovirus (Ad5) is a virus formed by an icosahedral protein capsid that encloses a linear DNA of 36 kilobases[8]. In adults infection with Ad5 is usually asymptomatic, and in children it causes a common cold and conjunctivitis. In general, Ad5 infects epithelial cells, which during a natural infection are the cells of the bronchial epithelium. It enters the cells by means of interaction of the fiber, a viral protein that extends like an antenna from the twelve vertices of the capsid, with a cell protein involved in intercellular adhesion called Coxsackie-Adenovirus Receptor (CAR). When the viral DNA arrives inside the nucleus, methodical transcription of the early viral genes begins. The first viral genes expressed correspond to the genes of the early 1A (E1A) region. E1A bonds with an Rb cell protein that is forming a complex with the E2F transcription factor. Thus, E2F is released to activate the transcription of other viral genes such as E2, E3 and E4 and cell genes that activate the cell cycle. Also, E1B bonds with p53 to activate the cell cycle and prevent the apoptosis of the infected cell. E2 codifies for replication proteins of the virus, E3 for proteins that inhibit the antiviral immune response and E4 for proteins that transport viral RNA. The expression of these early genes leads to the replication of the viral DNA and once replicated, activates the promoter that regulates the expression of the late or structural genes that form the capsid.

Methods have been used to construct oncolytic adenoviruses: the selection of viral functions that are not necessary in tumor cells and the replacement of viral promoters with tumor-selective promoters[1]. In both strategies, the gene to be selected or regular gene belongs preferably to the E1 region, and in particular, affects E1a because it controls the expression of other viral genes. As for selections of viral functions, the protein E1b-55K has, for example, been eliminated. This protein inactivates p53 to induce in the infected cell the entry in phase S of the cell cycle and to prevent cell apoptosis. A mutated adenovirus in E1b-55K known as Onyx-015 has been used to treat tumors defective in p53 although with little clinical success owing to its low propagation capacity or oncolytic potency. Another mutation performed in the adenoviral genome to achieve selective replication in tumors affects the CR2 field of E1a. This E1a field mediates the bonding to proteins of the Retinoblastoma (Rb) family. pRb proteins block the transition of the Go/G1 phase to the S phase of the cell cycle, forming a complex transcription inhibitor along with E2F. When E1a bonds with a pRb, the E2F transcription factor of the pRb-E2F complex is released and E2F acts as a transcriptional activator of the genes responsible for moving on to the S phase and viral genes such as E2. The release of E2F is thus a key step in the replication of the adenovirus. In tumor cells, the cell cycle is out of control because pRb is absent or inactivated by hyperphosphorylation and E2F is free. In these cells, the inactivation of pRb by E1a is now not necessary. Thus, an adenovirus with a mutation in E1a called Delta-24 that prevents its bonding with pRb can be propagated normally in cells with inactive pRb[9,10].

With regard to the strategy of replacing viral promoters with tumor-selective promoters, the E1a promoter has been replaced by various promoters such as the alpha-fetoprotein promoter, a prostatic-specific antigen (PSA), kallikrein, mucine 1 and osteocalcin[11-15]. However, a major problem has been identified in the use of cell promoters in the viral context: the existence of viral sequences that interfere with the proper regulation of the promoter and reduce selectivity[16,17]. It has been attempted to correct this loss of selectivity by regulating other viral genes as well as E1a, such as E1b, E2 and E4[18,19]. The regulation of various viral genes can be done with a different promoter for each viral gene, for example the E2F1 promoter for E1a and the telomerase promoter for E4. In this case, the two promoters must be expressed at high levels to allow viral replication such that oncolytic potency can remain reduced in many tumor cells[20]. Alternatively, two viral genes can be regular with the same promoter, for example in the oncolytic adenovirus Onyx 411, in which E1a and E4 are regulated by the E2F1 promoter[21]. However, it has been demonstrated that the duplication of promoter sequences in the adenoviral genome causes genomic instability by recombination between these repeated sequences[22]. This problem is difficult to solve because any modification of the E4 region seems to cause genomic instability of the oncolytic adenovirus[22]. In addition, the transcriptional regulation of adenoviral genes is temporarily controlled such that E1a activates the expression of other early viral genes. This regulation is optimal for the viral cycle and is lost if the promoter of viral genes other than E1a is replaced by tumor-specific promoters. On the other hand, the problem of interference between viral sequences and the specific promoter used to control adenoviral replication is especially important when it is desired to regulate the transcription of E1a and E4, given that there are enhancers and localized origins of transcription in the terminal repetitions and in the adenovirus-packaging signal[23-25]. In the field of non-oncolytic vectors, this interference has been alleviated by the insertion between the promoter and these enhancers of isolating sequences derived from the HS4 locus of the B-globin gene of chickens[26,27]. The insulating mechanism of HS4 is based on the protein CTCF union which inhibits the interactions between factors present in the enhancer and the promoter28. This invention describes the use of an insulating sequence derived from the human genome in the context of the oncolytic adenovirus design."

A particularly interesting promoter used in the design of oncolytic adenoviruses is the E2F1 promoter[20,21,29,30]. This promoter presents two E2F bonding sites. The family of E2F transcription factors regulates the transcription of genes that allow entry to the S phase of the cell cycle. These factors serve as activators when they are released and as repressors when they bond with the pRb retinoblastoma protein[31]. The bonding of pRb to E2F is regulated by phosphorylation of pRb such that the phosphorylation of pRb prevents its bonding with E2F. Tumors present alterations in the signal-translation routes that result in the hyperphosphorylation of pRb and an increase in free E2F. Thus, in tumors, genes are expressed that respond to E2F such as the E2F1 gene. On the other hand, in a normal quiescent cell, pRb is not phosphorylated and remains bonded to E2F, forming a complex that acts as a transcriptional repressor. In oncolytic adenoviruses, however, the simple regulation of E1a with the E2F1 promoter results in a low level of selective replication in tumors, of the order of 10 times[20]. The regulation of other viral genes in addition to E1a is a possible solution to this low selectivity, but presents the problems described in the paragraph above. For example, OAS403 is an oncolytic adenovirus with E1a regulated with the promoter of E2F1 and E4 regulated with the promoter of telomerase, which furthermore includes a polyadenylation signal to eliminate transcription from the ITR (inverted terminal repetition) and in which the packaging signal has been relocated to the extreme right of the genome to reduce interference with the E1a promoter[20]. During the amplification of OAS403, it has been seen that the packaging signal and sequences adjacent to E4 change position in the genome[22]. It has moreover been described that even minor modifications of the E4 region cause genomic instability, and so strategies based on modification of the E4 region have been abandoned[22]. Another problem found with the E2F1 promoter apart from its selectivity is the lack of potency. In addition to being not very selective, an oncolytic adenovirus with E1a regulated by the E2F1 promoter loses its lytic capacity with regard to the salvage adenovirus as shown by Ryan et al.[20] and in the examples presented in this invention.

This invention describes the use of appropriate DNA sequences to achieve the correct functioning of a genome promoter of an oncolytic adenovirus. With these sequences, an oncolytic adenovirus is designed that presents greater selectivity and anti-tumor potency. The use of the elements described in this invention allows the attainment of a high tumor selectivity and oncolytic capacity using only a tumor-specific promoter. The use of a single promoter reduces the problems of genomic instability associated with the repetition of the same promoter in the adenoviral genome. In addition, the regulation of only E1a, avoiding the regulation of other viral genes, allows the correct temporal regulation of adenoviral genes and prevents the genomic instability associated with modification of the E4 region.

SUMMARY

This invention refers to an oncolytic adenovirus for cancer treatment that contains a human DNA sequence isolating a promoter that confers selective expression on an adenoviral gene. In particular, the human DNA sequence is a sequence derived from the locus of myotonic dystrophy.

It also refers to an oncolytic adenovirus in which said adenovirus contains a sequence that optimizes the protein translation of an adenoviral gene regulated by a promoter that confers tumor selectivity. In particular, this sequence is the Kozak sequence.

Another object of the invention is an oncolytic adenovirus for cancer treatment that contains a human DNA sequence isolating a promoter of selective expression that regulates an adenoviral gene and a sequence that optimizes the protein translation of the same adenoviral gene. In particular, the human DNA sequence is a sequence derived from the locus of myotonic dystrophy.

Another object of this invention is an adenovirus that contains a human DNA sequence isolating a promoter of selective expression that regulates an adenoviral gene and a sequence that optimizes the protein translation of the same adenoviral gene and that also presents mutations in one or more genes of the E1a, E1b and E4 group to achieve selective replication in tumors. In particular, the human DNA sequence is a sequence derived from the locus of myotonic dystrophy.

Yet another object of this invention is an oncolytic adenovirus that contains a human DNA sequence isolating a promoter of selective expression that regulates an adenoviral gene and a sequence that optimizes the protein translation of the same adenoviral gene and modifications in its capsid to increase its infectivity or to direct it to a receptor present in a tumor cell. In particular, the human DNA sequence is a sequence derived from the locus of myotonic dystrophy.

Yet another object of this invention is an oncolytic adenovirus that contains a human DNA sequence isolating a promoter of selective expression that regulates an adenoviral gene and a sequence that optimizes the protein translation of the same adenoviral gene and that said adenovirus, in turn, contains other genes commonly used in the field of cancer gene therapy as prodrug activators, tumor suppressors or immunostimulators. In particular, the human DNA sequence is a sequence derived from the locus of myotonic dystrophy.

Yet another object of this invention is an oncolytic adenovirus that contains a human DNA sequence isolating a promoter of selective expression that regulates an adenoviral gene and a sequence that optimizes the protein translation of the same adenoviral gene where the adenovirus is a human adenovirus derived from a serotype between 1 and 50. In particular, the adenovirus is a human adenovirus serotype 5. In particular, the human DNA sequence is a sequence derived from the locus of myotonic dystrophy.

Yet another object of this invention is an oncolytic adenovirus that contains a human DNA sequence isolating the promoter of the modified human E2F1 gene by the addition of sites for bonding to E2F to regulate the expression of an adenoviral gene and a sequence that optimizes the protein translation of the same gene. In particular, the human DNA sequence is a sequence derived from the locus of myotonic dystrophy.

Another object of this invention is a pharmaceutical composition that includes an effective quantity of an oncolytic adenovirus that contains a human DNA sequence isolating a promoter of selective expression that regulates an adenoviral gene and a sequence that optimizes the protein translation of the same adenoviral gene and one or more pharmaceutically acceptable carriers and excipients. In particular, the human DNA sequence is a sequence derived from the locus of myotonic dystrophy.

Another object of this invention is the use of an oncolytic adenovirus that contains a human DNA sequence isolating a promoter of selective expression that regulates an adenoviral gene and a sequence that optimizes the protein translation of the same adenoviral gene for the preparation of a drug for the treatment or prevention of cancer or a premalignant condition thereof. In particular, the human DNA sequence is a sequence derived from the locus of myotonic dystrophy.

The adenovirus of this invention may optionally be combined with other methods of cancer treatment such as chemotherapy or radiotherapy.

This invention describes an oncolytic adenovirus that contains a human DNA sequence, in particular a sequence derived from the locus of myotonic dystrophy, as a sequence isolating a promoter of selective expression that regulates an adenoviral gene and, in turn, contains a sequence that optimizes the protein translation of the same adenoviral gene, as well as the use of said oncolytic adenovirus for the treatment or prevention of cancer or a premalignant condition thereof. Previously, the use of isolating sequences derived from B-globin of chickens in adenoviral vectors has been described[26,27]. Unlike in this invention, the isolators described previously are not of human origin and have not been used in a context of oncolytic adenoviruses. The locus of myotonic dystrophy is located in the human chromosome 13 in the position 19q13.3. This locus contains two bonding sites for the CTCF protein and a variable number according to each individual of CTG repetitions that jointly function as a potent isolator of the effect of enhancers or activators on promoters[32]. Prior to this invention, its activity had never been analyzed in a viral genome. Its activity in a viral genome is not obvious, as its activity has been demonstrated only in the context of a cell chromosome in which the associated histones can play a role in its functioning. Its human origin offers a superior alternative to the use of the HS4 sequence of chickens as the transfer of sequences of non-human origin can have biosafety implications.

In addition, this invention describes the use of an optimized sequence for protein translation to increase the levels produced of the adenoviral protein regulated below the tumor-specific promoter. The regulation of the expression of a viral gene with a tumor-selective promoter presents the disadvantage that the level of expression is usually lower than the level of expression observed in Ad5. This lower expression results in lower replicative potency of the oncolytic adenovirus. Insertion of the Kozak sequence at the beginning of translation of the gene regulated by the selective promoter is capable of restoring the levels of expression of the gene regulated.

This invention also describes the strategy of increasing the number of binding sites at E2F in the sequence of the human promoter E2F1 to better control the expression of E1a in an oncolytic adenovirus. This increase in binding sites at E2F produces greater expression of E1a in tumor cells and reduced expression of E1a in normal cells, resulting in an increase in tumor selectivity of adenoviral replication.

The invention is directed towards the need to find better treatments for cancer, including, but not limited to, cancer of the pancreas, colon and lung. Cancer treatment with the oncolytic adenovirus that contains the human DNA sequence and the sequence that optimizes protein translation can be performed by direct injection inside the tumor or by systemic intravenous injection in patients suffering from cancer using standard methods in the field of gene therapy and virotherapy with adenoviruses.

DRAWINGS

This patent or application file contains at least one drawing executed in color. copies of this patent or patent application publication with color drawing(s) will be provided by the office upon request and payment of the necessary fee.

The drawings presented herein further describe the present invention. These drawings are part of the specifications and illustrate certain embodiments of the present invention, but should not be considered restrictive of the scope of the invention.

FIG. 1. Structure of adenovirus expounded in this invention. The arrows indicate the modifications most representative of each virus regarding parental versions. Adwt is the wild virus with no modification. It shows inverted terminal regions (ITR) for its replication and a packaging signal (Ψ) together with ITR on the left. In addition, the position of the early gene E1a and its promoter are indicated. The virus AdwtRGD coincides with Adwt but also contains the tripeptide sequence RGD (Arginine-Glycine-Aspartic Acid) in the sequence of the viral fiber. This sequence serves to bind 5 integrins that are overexpressed in the membrane of tumor cells. This virus is used as a positive control of replication. The virus Ad-Δ24RGD is similar to AdwtRGD but has a deletion of 24 nucleotides, corresponding to 8 amino acids, in the binding site of E1a to pRB. Said deletion prevents the separation of complex pRB-E2F present in quiescent normal cells so that said virus is preferentially replicated in cells in division or tumor cells. This virus is used to compare the level of selectivity of the viruses described in this invention. The Ad-TLRGD virus is a virus similar to AdwtRGD but with the E1 region replaced by luciferase genes and green fluorescence protein (GFP) genes. This virus because it lacks the E1 region cannot be replicated and is used as a negative control. The ICOVIR viruses are derived from Ad-Δ24RGD by the substitution of the E1a promoter by a selective activation promoter in tumors, promoter E2F1. Thus ICO-VIR1 is similar to Ad-Δ24RGD but contains said substitution. This virus is used as a control of E1A expression, controlled by promoter E2F1 in the absence of insulating sequences of the promoter. ICOVIR2 is similar to ICOVIR1 but contains a sequence of the myotonic dystrophy locus at promoter E2F1. ICOVIR5 also contains the Kozak sequence in the beginning of translation of E1a in order to optimize its translation and thus increase the levels of expression of E1a in tumor cells. ICOVIR7 also has two additional binding sites to E2F in the E2F1 promoter. The ICOVIR2, 5 and 7 viruses serve to demonstrate the object of this invention: the best gene regulation when the DM insulating sequence is used.

Figure 2:
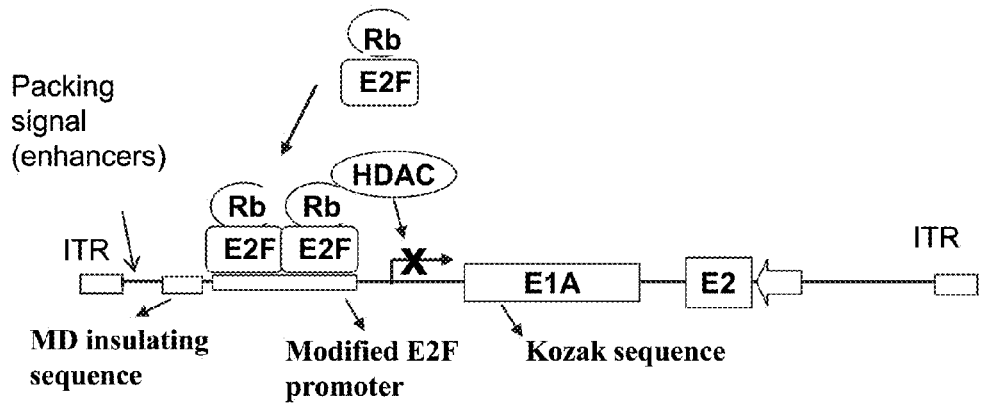
Figure 2:
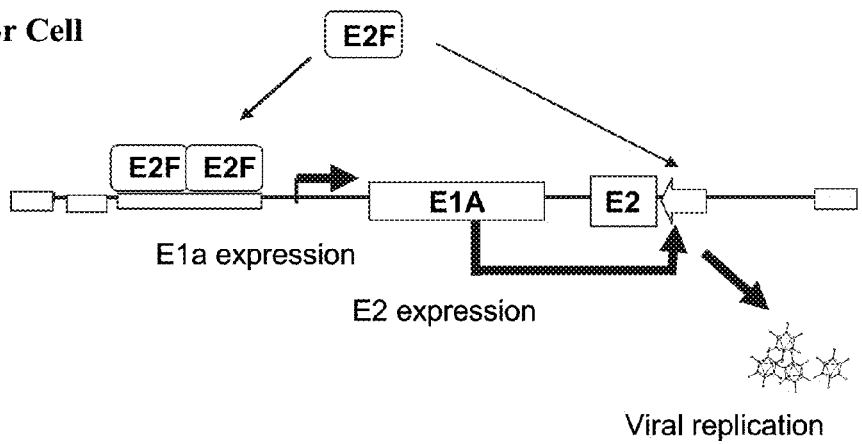

FIG. 2. Diagram of the functioning of oncolytic adenoviruses containing the DM sequence of the myotonic dystrophy insulating locus at promoter E2F1 that regulates E1a. The oncolytic viruses ICOVIR2, 5 and 7 contain promoter E2F1 insulated with the DM sequence. In ICOVIR5 and 7, the first codon of the E1a sequence is preceded by the Kozak sequence (CCACC) to optimize protein translation. In addition, in ICOVIR7 the promoter of E2F1 is modified by the insertion of additional binding sites to E2F to increase its potency and selectivity. In a normal cell, complex pRB E2F acts as a repressor of the promoter of E2F1 through the action of histone deacetylases (HDAC) and E1a is not expressed. In a tumor cell, pRB is hyperphosphorylated or absent and E2F is free. In this manner it acts as a transcriptional activator of E1a. The Kozak sequence preceding E1a allows a correct level of expression of E1a. The insulating DM avoids the interference of the ITR and adenoviral packaging signal in the modified E2F1 promoter.

Figure 3:
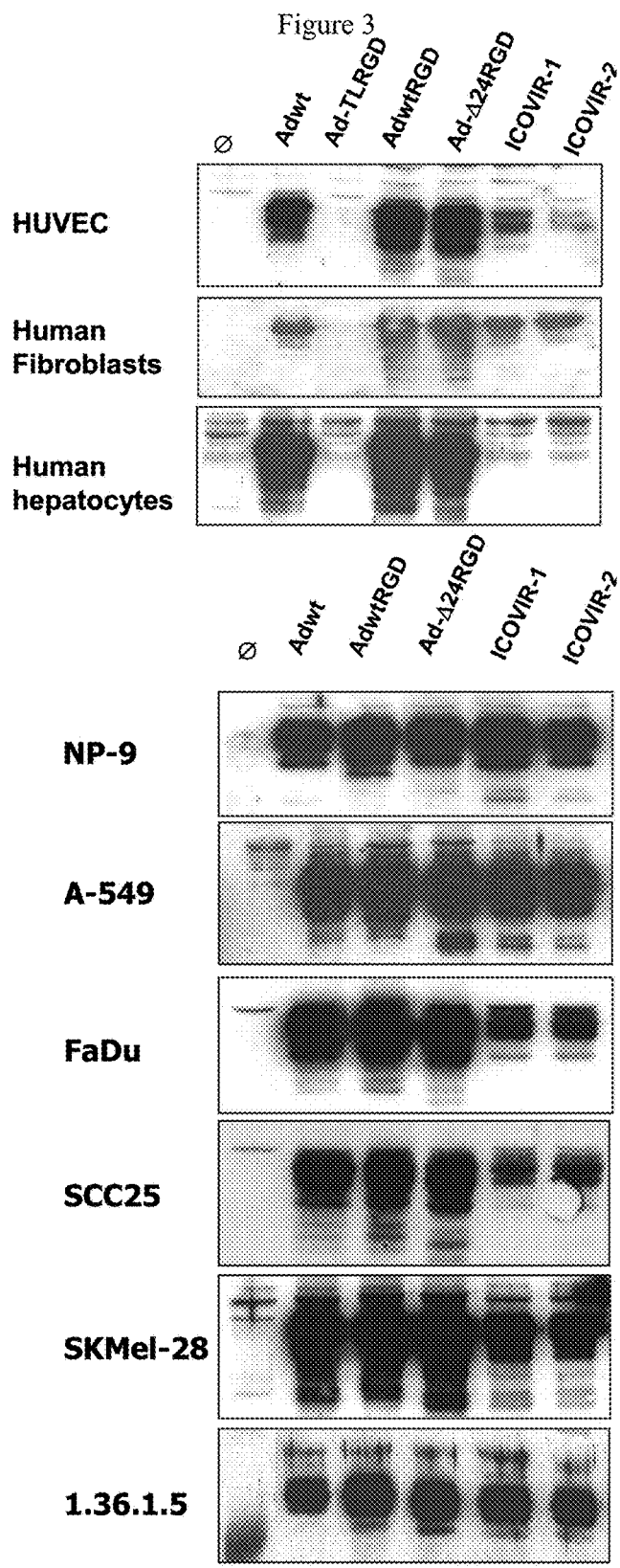

FIG. 3 demonstration of the effect on the expression of E1a resulting from the insertion of a DM insulating sequence in front of the E2F1 promoter.

Endothelial cells from human umbilical cord (HUVEC), human fibroblasts and human hepatocytes are used as controls of non-tumor cells. The cell lines NP-9 (adenocarcinoma of the pancreas), A-549 (adenocarcinoma of the lung), FaDu (head and neck tumors), SCC25 (head and neck tumors), SKMel-28 (melanoma) and 1.36.1.5 (melanoma) are used as a model of the human tumor cell. These cells were infected with Adwt and AdwtRGD (positive controls of non-selective expression of E1a), and oncolytic viruses Ad-Δ24RGD (non-selective expression of E1a-D24), ICO-VIR1 (E1a controlled by promoter E2F1) and ICOVIR2 (E1a controlled by promoter E2F1 insulated with the DM sequence, object of this invention). O represents a cellular extract of uninfected cells. For normal cells a negative control of infection is also shown with virus Ad-TLRGD which has region E1 replaced by luciferase genes and green fluorescence protein (GFP) genes. This negative control shows no expression of E1a. After 24 hours the cells were read and E1a was detected by Western Blot. The presence of promoter E2F1 (ICOVIR1) is capable of reducing the expression of E1a in normal cells. Additionally, in HUVEC normal cells, it is observed that the DM sequence confers greater control over the expression of E1a by the promoter E2F1 (column ICOVIR2 compared with column ICOVIR1). In both ICOVIR1 and ICOVIR2 tumor cells, they are capable of expressing E1a, but in FaDu, SCC25 and SKMel-28, the expression of E1a in cells infected with ICOVIR1 or ICOVIR2 is lower than that obtained with the adenovirus where E1a is not regulated by E2F1 (virus Adwt, AdwtRGD and Ad-Δ24RGD). This indicates that the promoter of E2F1, insulated or not with DM, does not have the power required to allow a level of expression of E1a in tumor cells comparable to wild adenovirus. As shown below, this invention solves this problem with insertion of the Kozak sequence in E1a (in ICOVIR5) and modification of the promoter E2F1 (in ICOVIR7).

Figure 4:
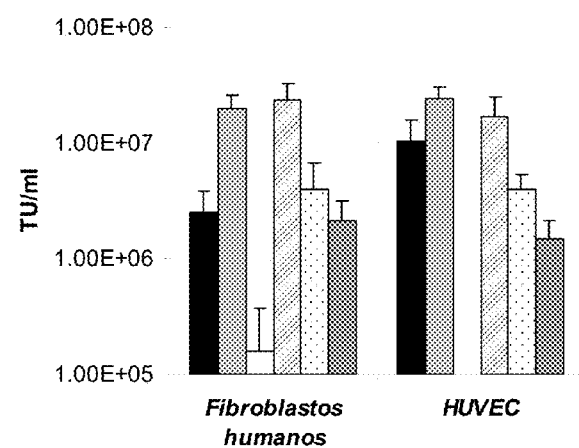
Figure 4:
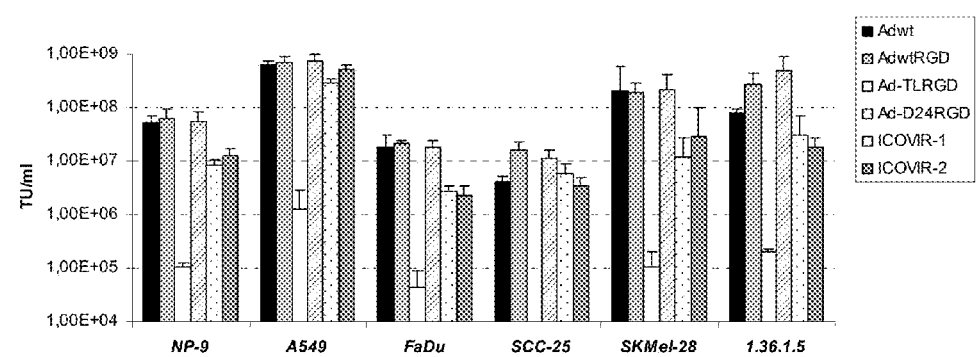

FIG. 4. The DM sequence allows for an increase in antitumor selectivity of an oncolytic adenovirus with E1a regulated with the promoter of E2F1.

To demonstrate that an oncolytic adenovirus with E1a regulated with the promoter of E2F1 insulated with the DM sequence is selectively replicated in tumor cells, we proceeded to infect human fibroblasts and endothelial cells from human umbilical cord (HUVEC) with Adwt (positive control of non-selective expression of E1a) and AdwtRGD (positive control of infectivity increased by the RGD sequence and non-selective expression of E1a), Ad-TLRGD (negative control of non-replicative, due to lack of E1a, virus), and oncolytic viruses Ad-Δ24RGD (expression of non-selective E1a-Δ24RGD), ICOVIR1 (E1a controlled by promoter E2F1) and ICOVIR2 (E1a controlled by promoter E2F1 insulated with the DM sequence). Five days post-infection the cells and their culture media were collected, and they underwent three freeze-thaw cycles to release the virus (viral extract). The amount of virus in the cell extract was determined by infection of a monolayer of HEK293 cells and subsequent staining with the monoclonal antibody 2Hx-2 (ATCC) that recognizes the adenoviral hexon and a mouse anti-IgG secondary antibody, Alexa 488 (Molecular Probes, Eugene, Oreg.). The monolayer was observed under fluorescence microscope and every fluorescent cell was quantified as a transduction unit (TU). Thus, the number of units per milliliter of viral extract was determined. The bars show said number of units of transduction per milliliter of viral extract. The presence of the DM insulating sequence in ICOVIR2 results in a lower viral replication in normal fibroblasts and HUVEC compared with ICOVIR1 which has the non-insulated promoter E2F1. Below is the same experiment using monolayers of tumor cells NP-9 (adenocarcinoma of the pancreas), A-549 (adenocarcinoma of the lung), FaDu (head and neck tumors), SCC25 (head and neck tumors), SKMel-28 (melanoma) and 1.36.1.5 (melanoma). In most tumor lines, the replicative capacity of ICOVIR1 and ICOVIR2 measured in transduction units per milliliter (TU/ml) is greater than the negative control Ad-TLRGD but lower than that of the positive controls Adwt and AdwtRGD. As shown below in FIGS. 5, 6 and 7, this invention describes the method to preserve the selectivity provided by promoter E2F1 insulated with DM by increasing the replicative capacity via the insertion of the Kozak sequence in E1a and modification of promoter E2F1.

Figure 5:
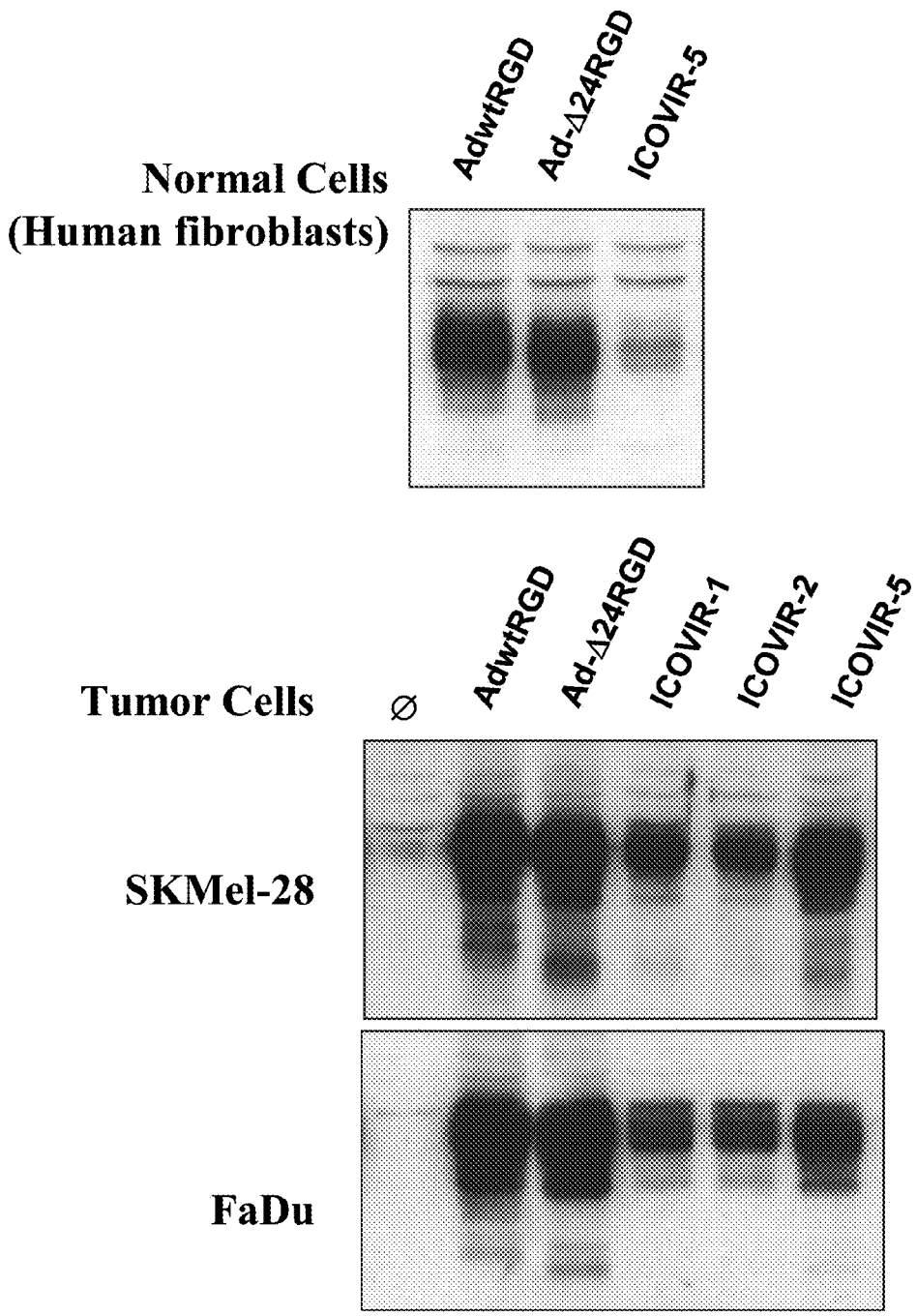

FIG. 5 Effect of inserting the Kozak sequence to increase the power of the promoter insulated with DM.

Human fibroblasts were infected with AdwtRGD (positive control of infectivity increased by the RGD sequence and non-selective expression of E1a) and oncolytic viruses Ad-Δ24RGD (non-selective expression of E1a-ΔA24), and ICOVIR5 (E1a preceded by the Kozak sequence and controlled by promoter E2F1 insulated with the DM sequence). After 24 hours the cells were read and E1a was detected by Western blot. The band corresponding to E1a in fibroblasts infected with ICOVIR5 is less intense than that for fibroblasts infected with the control virus. Below is the same experiment performed with melanoma tumor cells (SK-Mel28) and head and neck tumors (FaDu). In addition to the positive controls AdwtRGD and Ad-Δ24RGD, in which E1a is not controlled by a tumor selective promoter and a negative control of uninfected cells (O), immunostaining is seen of the extracts of cells infected with ICOVIR1 (E1a controlled by promoter E2F1), ICOVIR2 (E1a controlled by promoter E2F1 insulated with DM sequence) and ICOVIR5 (E1a preceded by the Kozak sequence and controlled by the promoter E2F1 insulated with the DM sequence). The level of expression of E1a is higher in ICOVIR5 than in ICOVIR2, which demonstrates the effect of the Kozak sequence to increase the power of the promoter insulated with DM.

Figure 6:
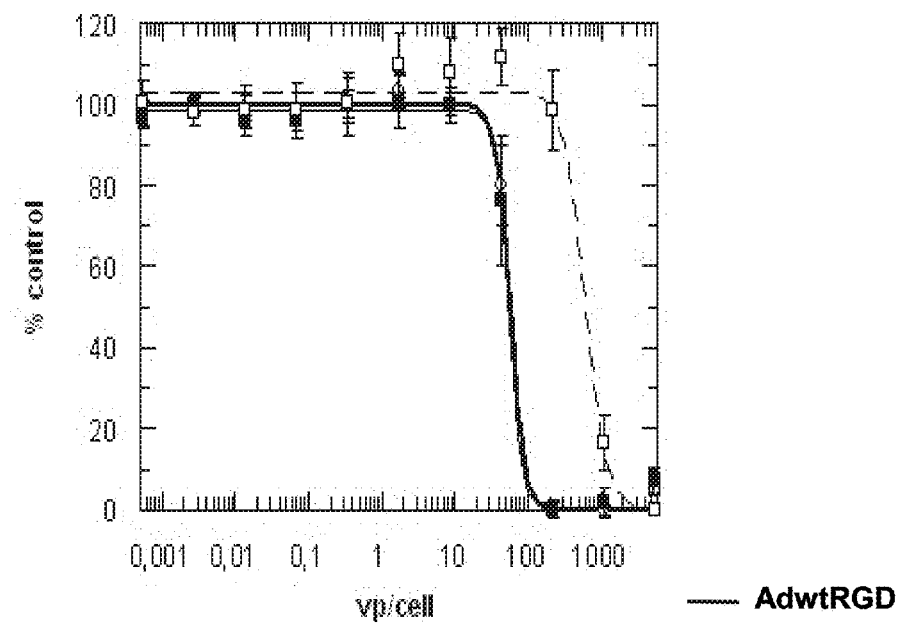
Figure 6:
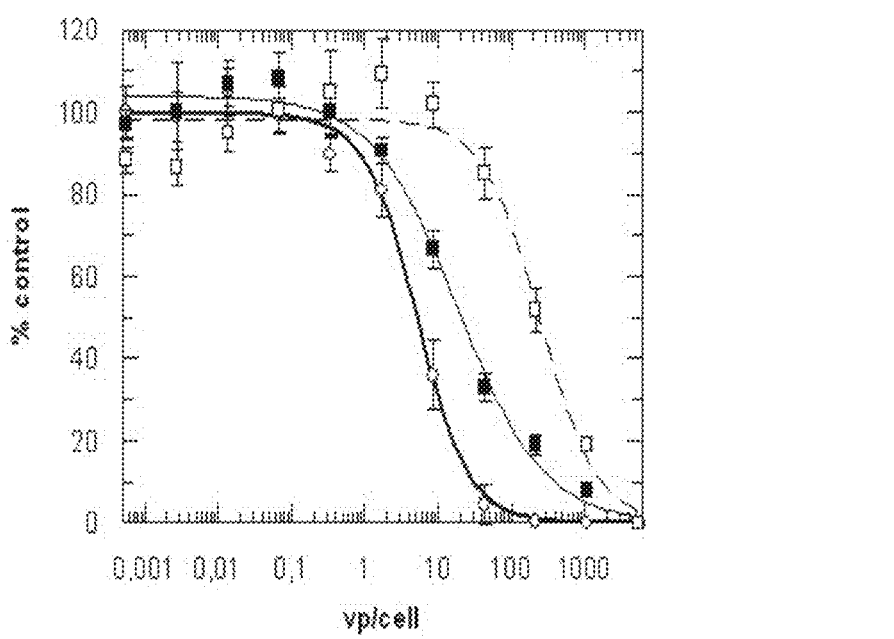

FIG. 6. In vitro oncolytic effectiveness of adenoviruses containing E1a regulated with the promoter of E2F1 insulated with the DM sequence and the Kozak sequence to optimize translation of E1a.

Cells from the melanoma tumor line SKMel28 or head and neck tumor FaDu were cultured in wells from a plate of 96 wells (3000 cells per well) and were infected with increasing concentrations of AdwtRGD (positive control of infectivity increased by the RGD sequence and non-selective expression of E1a), ICOVIR2 (E1a controlled by the promoter E2F1 insulated with the DM sequence), or ICOVIR5 (E1a preceded by the Kozak sequence and controlled by the promoter E2F1 insulated with the DM sequence). The X-axis shows the concentration of viral particles per cell (vp/cell) used in the initial infection. After five days the monolayer of infected cells was washed with saline buffer and the amount of cells remaining in the well was measured by quantifying the total protein remaining in the well (BCA method[33]). The cytopathic effect (CPE) induced by the virus is seen as a decrease in the amount of protein in the cell monolayer infected. The result is indicated as a percentage with respect to an uninfected well. The sooner the curve drops, the greater the cytolytic effect of the virus. Overall, the results show that ICOVIR5 has a greater lytic capacity than ICOVIR2, which shows the enhancing effect conferred by the Kozak sequence.

Figure 7:
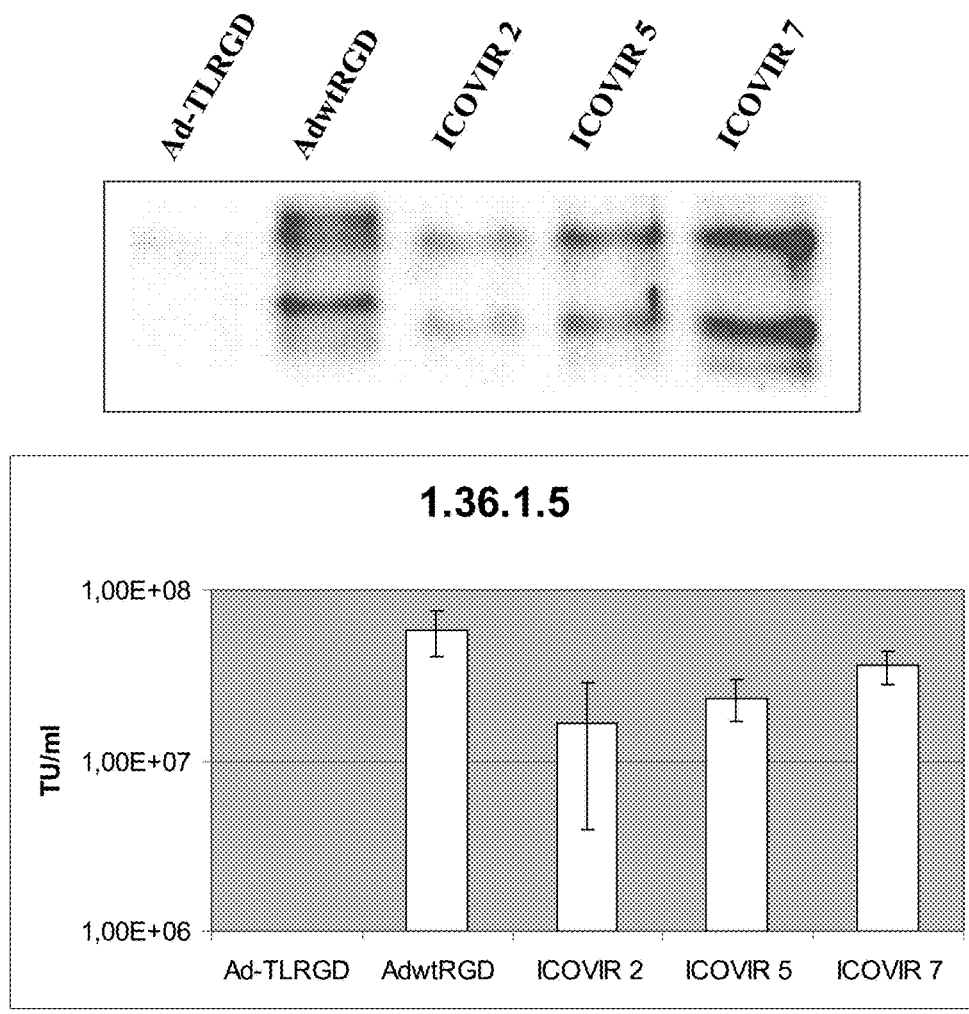

FIG. 7. Effect of modification of E2F1 promoter to increase its power when it is insulated with the DM sequence.

Cells of the melanoma tumor line 1.36.1.5. were infected with Ad-TLRGD (non-replicative negative control of virus for lack of E1a), AdwtRGD (positive control of infectivity increased by the RGD sequence and non-selective expression of E1a), and oncolytic viruses ICOVIR2 (E1a controlled by the E2F1 promoter insulated with the DM sequence), ICOVIR5 (E1a preceded by the Kozak sequence and controlled by the promoter E2F1 insulated with the DM sequence) and ICOVIR7 (E1a preceded by the Kozak sequence and controlled by a promoter E2F1 modified by two additional binding sites to E2F and insulated with the DM sequence). After 24 hours the cells were read and E1a was detected by Western blot. The band corresponding to E1a in melanoma cells infected with ICOVIR7 is of greater intensity than that corresponding to the same cells infected with ICOVIR2 and ICOVIR5 and similar to that present in cells infected with the control virus AdwtRGD. This demonstrates the enhancing role of the additional binding sites to E2F in ICOVIR7.

Below is the same experiment but instead of performing a cellular extract the day following the infection, we waited five days post-infection and collected the cells and their culture media. This supernatant and cell mixture underwent three freeze-thaw cycles to release the virus (viral extract). The amount of virus in the cell extract was determined by infection of a monolayer of HEK293 cells and subsequent staining with the monoclonal antibody 2Hx-2 (ATCC) that recognizes the adenoviral hexon and a mouse anti-IgG secondary antibody, Alexa 488 (Molecular Probes, Eugene, Oreg.). The monolayer was observed under fluorescence microscope and every fluorescent cell was quantified as a transduction unit (TU). Thus, the number of transduction units per milliliter (TU/ml) of viral extract was determined. As a control of maximum production the virus AdwtRGD is used, in which E1a is not regulated. ICOVIR7 is capable of propagating with the same power as the control AdwtRGD.

Figure 8:
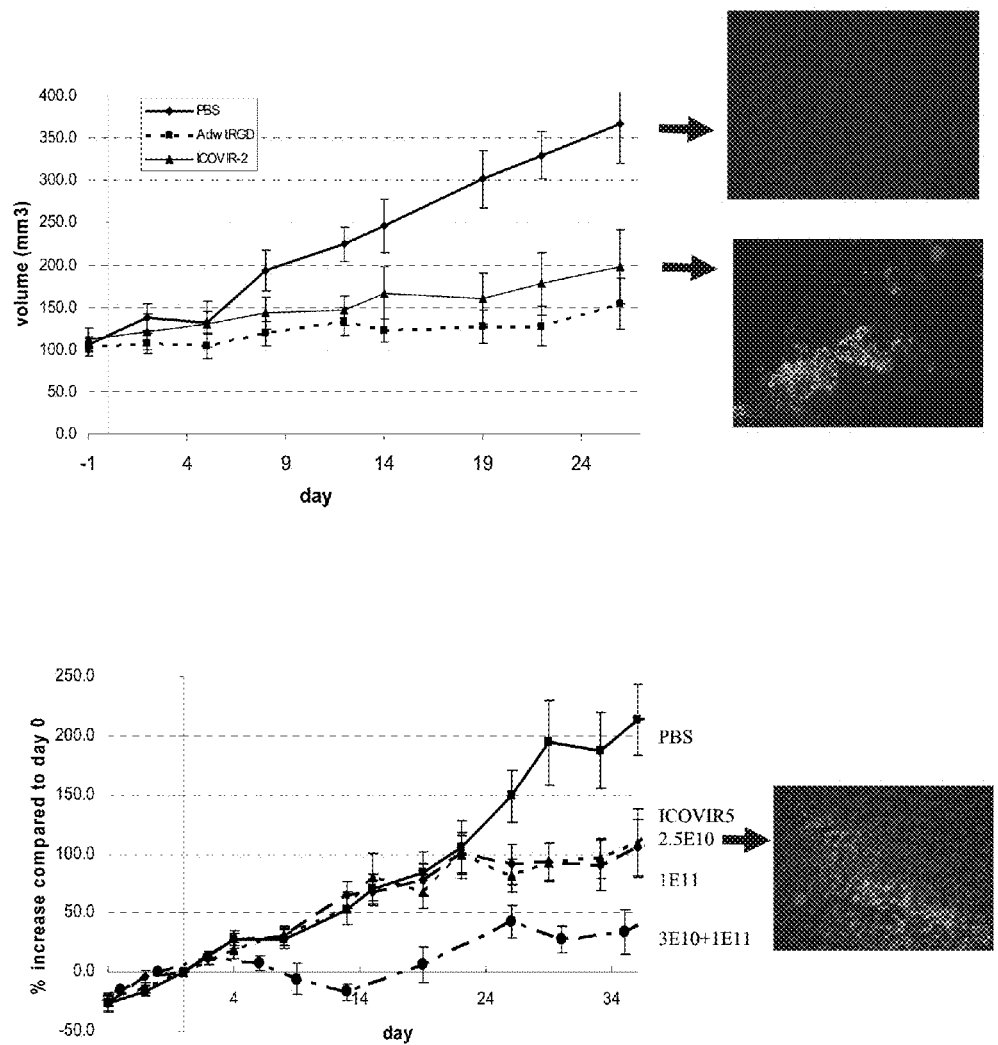

FIG. 8. An adenovirus containing E1a regulated with promoter E2F1 insulated with the DM sequence and Kozak sequence at the beginning of translation of E1a can be used to treat tumors.

The top of the figure shows an experiment in vivo with athymic mice of the BALB/c strain containing NP9 tumors. A total of $1.2 \times 10^7$ tumor cells were injected subcutaneously in the back of each flank of the mouse. After 15 days the tumors formed (which reached 70-80 mm$^3$) were distributed in different experimental groups (n=10 per group). The tumors were injected with PBS (♦) or $10^9$ viral particles of ICOVIR-2 (▲) or AdwtRGD (■). The graph shows the evolution of tumor volume. ICOVIR2 can inhibit tumor growth. The photographs show staining of a section of tumor in each group with monoclonal antibody 2Hx-2 (ATCC) that recognizes the adenoviral hexon and a mouse anti-IgG secondary antibody Alexa 488 (Molecular Probes, Eugene, Oreg.). The presence of virus is observed in a tumor treated with ICOVIR-2 (bottom panel) given its absence in another tumor treated with PBS (top panel). Below is a systemic intravenous treatment with ICOVIR5 of mice with subcutaneously implanted melanoma tumors SKMel-28. Treatments: PBS (■). One injection on day 0 of ICOVIR-5 of $2.5 \times 10^{10}$ viral particles (vp) (▲). One injection on day 0 of ICOVIR-5 from $1.10^{11}$ vp (♦). One injection on day 0 of $3.10^{10}$ vp and another of $1.10^{11}$ vp separated by 1 hour (•). The average tumor growth of 8-10 tumors/group±S.E. is represented. The change over time of the percentage of tumor volume with respect to day 0 is indicated. All treatment regimens with ICOVIR-5 showed oncolytic activity resulting in a suppression of tumor growth significantly different than the control group (PBS), p<0.05. The photograph shows the presence of virus in the tumor treated with ICOVIR5.

Figure 9:
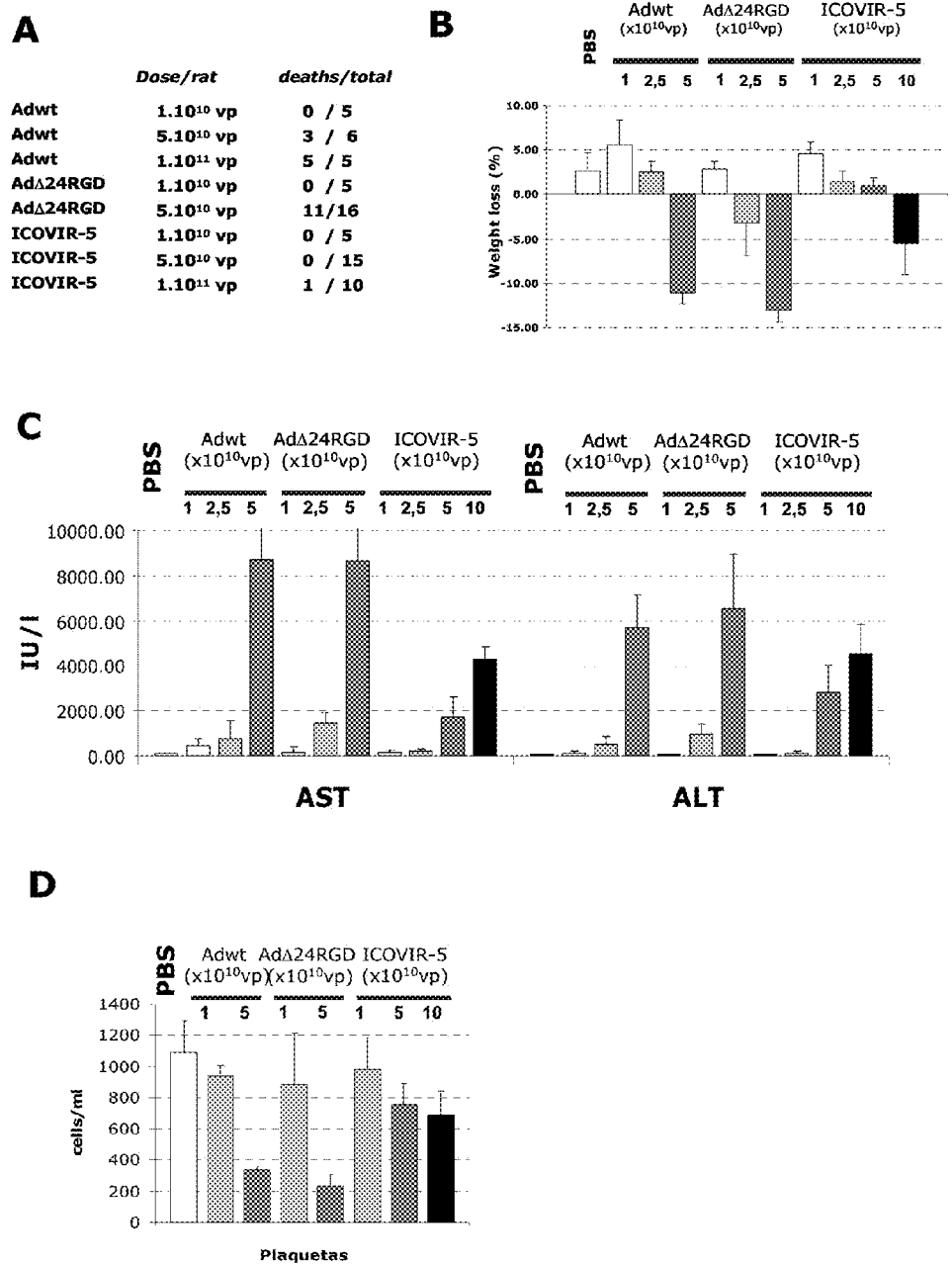

FIG. 9. Demonstration in vivo of the reduction of toxicity after intravenous injection of adenovirus containing regulated E1a with the promoter of E2F1 insulated with the DM sequence and the Kozak sequence to optimize translation of E1a.

The toxicity in vivo of an adenovirus containing the Kozak sequence in E1a and a promoter E2F1 insulated by DM (ICOVIR5) was compared with that of the wild virus Adwt and the oncolytic virus Ad-Δ24RGD expressing E1a under its natural promoter. The viruses were administered intravenously at different doses ($10^{10}$, $5 \times 10^{10}$ and $10^{11}$) in immunocompetent Balb/c mice. For 3 days post-injection, parameters associated with toxicity were evaluated. A shows the number of deaths with respect to the number of animals treated. This mortality includes animals sacrificed for having a weight loss equal to or greater than 20%. B represents the percentage variation in body weight for each group of animals treated with the control vehicle (PBS) or different viruses at the doses indicated. C shows the international units (IU) of serum transaminases aspartate aminotransferase (AST) and alanine-aminotranferase (ALT) per liter of blood plasma detected after the intravenous injection of the control vehicle or the viruses indicated at the doses indicated. D shows the number of platelets per milliliter of blood detected after intravenous injection of the control vehicle or the viruses indicated at the doses indicated. For each of these parameters the toxicity associated with the administration of ICOVIR 5 is very low even at the highest dose.

Figure 10:
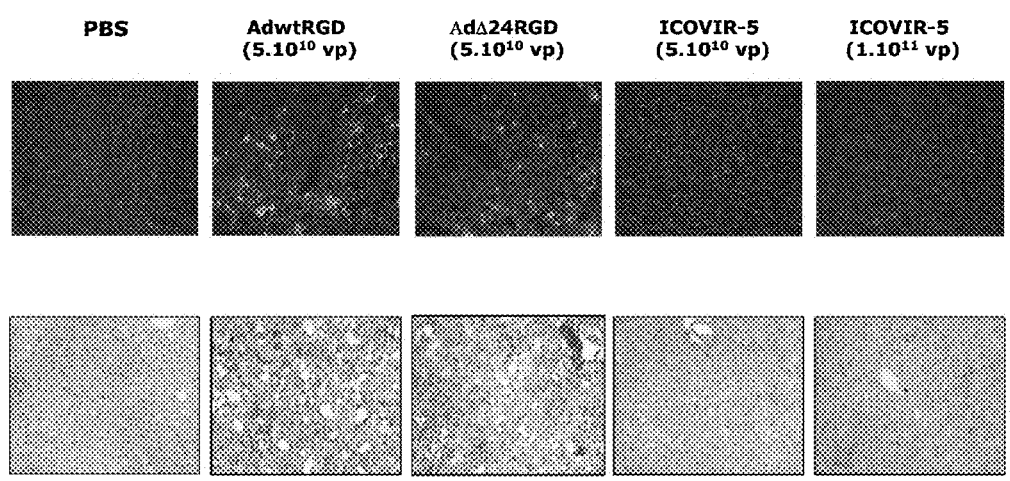

FIG. 10. Demonstration in vivo of reduction in the expression of E1a in non-tumor tissue and toxicity after intravenous injection of adenovirus containing E1a regulated with the promoter of E2F1 insulated with the DM sequence and the Kozak sequence to optimize the translation of E1a.

Immunocompetent Balb/c mice were treated with intravenous $5 \times 10^{10}$ virtual particles (vp) of AdwtRGD (positive control of infectivity increased by the RGD sequence and non-selective expression of E1a) and oncolytic viruses Ad-Δ24RGD (non-selective expression of E1a-Δ24), and ICOVIR5 (E1a preceded by the Kozak sequence and controlled by the promoter E2F1 insulated with the DM sequence). In the case of injection with ICOVIR5, a group of animals with a higher dose of $1 \times 10^{11}$ viral particles per mouse (right panels) was included. At 3 days post-injection the expression of E1a in liver sections by immunohistochemistry (upper panels) was evaluated. E1a was not detected in animals injected with ICOVIR5. The anatomopathologic evaluation of liver sections stained with eosin-hematoxylin indicates a normal appearance of the livers of mice injected with ICOVIR5 (lower panels).

DESCRIPTION

A. Structure of the adenoviruses that contain E1a regulated with the E2F1 promoter isolated with the DM sequence, the Kozak sequence to optimize E1a translation and the addition of sites for bonding to E2F in the E2F1 promoter.

This invention describes the use in cancer treatment of adenoviruses that contain E1a regulated with the E2F1 promoter isolated with the DM sequence, the Kozak sequence to optimize E1a translation and the addition of sites for bonding to E2F in the E2F1 promoter. The treatment is based on the selective replication of these viruses in tumors that have an altered retinoblastoma route.

The retinoblastoma route is the set of protein interactions that occur from the cell membrane up to the nucleus to regulate the level of phosphorylation of the protein of retinoblastoma pRb. Cancer is characterized by an alteration of this route such that the pRb protein is hyperphosphorylated or lost. This pRb alteration causes a loss of pRb bonding to the E2F transcription factor and an increase in free E2F in the nucleus of the tumor cells. This transcription factor bonds to the promoters with specific E2F bonding sites, as an E2F1 promoter, to increase its expression.

The selective-replication mechanism in tumors of adenoviruses containing E1a regulated with the E2F1 promoter isolated with the DM sequence, the Kozak sequence at the start of E1a translation and the addition of sites for bonding to E2F in the E2F1 promoter is based on the idea that the presence of free E2F in the tumors activates the expression of the E2F1 promoter in this virus and is indicated in FIG. 2 of this invention. The presence of the DM sequence enables correct activation of the promoter. The presence of the Kozak sequence enables synthesis of a quantity of E1a sufficient for maintaining the appropriate replicative and lytic capacity of the oncolytic virus. Likewise, the presence of additional sites for bonding to E2F in the E2F1 promoter enables an increase in the level of expression of E1a to maintain the appropriate replicative and lytic capacity of the oncolytic virus.

The DM insulating human sequence derived from the locus of myotonic dystrophy is represented by SEQ. ID 1 (from position 368 to 1096 of sequence 1). The DM sequence is characterized in that it contains two binding sites to factor CTCF and a variable number of repetitions of sequence CGT which function together as a powerful insulator against transcriptional interference[32]. In this invention, the DM sequence acts to insulate the effect of enhancers, located in the sequence of adenovirus packaging next to the promoter of E1a. The promoter of E1a is replaced by a selective promoter of tumors such as, for example, the promoter E2F1 and, to insulate this promoter from the enhancers present in the sequence of adenoviral packaging, the DM sequence is inserted between said sequence of packaging and promoter E2F1. The sequence of the promoter of E2F1 is shown in SEQ. ID 1 (from position 1283 until position 1564 of sequence 1). This promoter is characterized by having two binding sites to E2F organized in imperfect palindromes and four binding sites to Sp1[34]. In this invention the sequence of promoter E2F is modified by the insertion of binding sites to E2F in addition to those that already exist in the wild human promoter (from position 1321 until position 1447 of SEQ. ID 3). This is achieved by increasing both transcriptional repression in normal cells as well as transcriptional activation in tumor cells. The translation of mRNA by eukaryotic ribosomes can be optimized if we insert the sequence C C A/G C C in front of the first ATG codon translated[35]. This sequence was identified by Marylin Kozak and has received the name of Kozak. In this invention this sequence serves to compensate for the low power observed experimentally when a tumor selective promoter, such as promoter E2F1, insulated with the DM sequence, is used to control the expression of E1a (position 1546 until 1550 of SEQ. ID 2).

There are several ways to manipulate the adenoviral genome. The methods of construction of genetically modified adenoviruses are well established in the field of gene therapy and virotherapy with adenovirus[36-41]. The most commonly used method is based on first building the genetic modification desired into a plasmid that contains the adenoviral region to be modified, and then performing a homologous recombination in bacteria with a plasmid that contains the first of the viral genome[41]. This process can be as follows:

Other types of genetic mutation and manipulation different from regulating the expression of E1a with the E2F1 promoter isolated with the DM sequence, the insertion of the Kozak sequence to optimize E1a translation and the addition of sites for bonding to E2F in the E2F1 promoter described in this invention have been performed to obtain selective replication in tumors[1,42-44]. These may be insertions of other promoters different from E2F1 that are active in tumor cells and that are also used to control the expression of viral genes. A feature of this invention is the use of the DM isolating sequence and the Kozak sequence in combination with these other promoters.

Another modification described to achieve selective replication in tumors is the selection of early E1 functions that block the RB route. The selective replication of these mutants has already been demonstrated[9,10]. Other viral genes that interact directly with pRb such as E4[45] and E4orf6/7[46], respectively, are candidates for deletion to achieve selective replication in tumor cells.

In another feature of the invention, adenoviruses with the expression of a viral gene regulated by the selective promoter isolated with the DM sequence and potentiated with the Kozak sequence can contain modifications of their capsid to increase their inefficacy or be directed to receptors present in the tumor cell. The proteins of the adenoviral capsid have been genetically modified to include ligands that increase inefficacy or direct the virus to a receptor in the tumor cell[47-53]. Directing the adenovirus to the tumor can also be achieved with bifunctional ligands that bond to the virus on one side and to the tumor receptor on the other[53-56]. On the other hand, to increase the persistence of the adenovirus in blood and thus increase the possibilities of reaching disseminated tumor nodules, the capsid can be covered with polymers such as polyethylene glycol[57-60]. These modifications can be configured in adenoviruses that contain E1a regulated with the E2F1 promoter isolated with the DM sequence, the Kozak sequence at the start of E1a translation and the addition of sites for bonding to E2F in the E2F1 promoter.

Another feature of this invention is adenoviruses that contain E1a regulated with the E2F1 promoter isolated with the DM sequence, the Kozak sequence at the start of E1a translation and the addition of sites for bonding to E2F in the E2F1 promoter, but which are derived from other serotypes of adenoviruses other than Ad5.

Another feature of this invention refers to adenoviruses that contain E1a regulated with the E2F1 promoter isolated with the DM sequence, the Kozak sequence at the start of E1a translation and the addition of sites for bonding to E2F in the E2F1 promoter and that, in turn, contain other genes for increasing their cytotoxicity to tumor cells such as the gene of thymidine kinase, cytosine deaminase, proapoptotic genes, immunostimulators or tumor suppressors.

B. Production, purification and formulation of adenoviruses that contain E1a regulated with the E2F1 promoter isolated with the DM sequence, the Kozak sequence at the start of E1a translation and the addition of sites for bonding to E2F in the E2F1 promoter.

The adenoviruses described in this invention are propagated following standard methods in the fields of adenovirology and adenoviral vectors[36,37]. The preferred propagation method is by infection of a cell line permitting the replication of adenoviruses that contain E1a regulated with the E2F1 promoter isolated with the DM sequence, the Kozak sequence at the start of E1a translation and the addition of sites for bonding to E2F in the E2F1 promoter. The line of pulmonary adenocarcinoma A549 is an example of this line. Propagation is performed, for example, as follows: The A549 cells are grown on plastic plates for cell cultivation and infected using 50 viral particles per cell. Two days after the cytopathic effect that reflects the production of viruses is observed as a cluster of cells. The cells are collected and stored in tubes. After centrifugation at 1,000 rpm for 5 minutes, the cell precipitate is frozen and thawed three times to break the cells. The resulting cell extract is centrifuged at 1,000 rpm for 5 minutes and the supernatant with viruses is loaded above a gradient of caesium chloride and centrifuged for 1 hour at 35,000 rpm. The virus band in the gradient is reloaded above another gradient of caesium chloride and centrifuged for 16 hours at 35,000 rpm. The virus band is collected and dialyzed with PBS-10% glycerol. The dialyzed virus is aliquoted and stored at −80° C. The number of particles and plate-forming units is quantified following standard protocols[39].

A saline phosphate buffer with glycerol at 10% is a standard formulation for storing adenoviruses. However, new formulations have been described that improve the stability of the virus[61,62].

C. Use of adenoviruses that contain E1a regulated with the E2F1 promoter isolated with the DM sequence, the Kozak sequence at the start of E1a translation and the addition of sites for bonding to E2F in the E2F1 promoter for the treatment of cancer.

This invention describes the use of adenoviruses that contain E1a regulated with the E2F1 promoter isolated with the DM sequence, the Kozak sequence at the start of E1a translation and the addition of sites for bonding to E2F in the E2F1 promoter for the treatment of cancer. The treatment is based on the selective replication of these viruses in cells with an active RB route.

The protocols for using the viruses described in this invention in the treatment of cancer follow the same procedures as those used in the fields of virotherapy with adenoviruses and gene therapy with adenoviruses. There is wide experience in the use of non-replicative and replicative adenoviruses in the field of gene therapy. In particular, adenoviruses with selective-replication methods other than that proposed in this invention have been used to treat cancer[9,37,63-68]. There are numerous publications dealing with treatment of tumor cells in cultivation, animal models and clinical trials with human patients. For the treatment of cells in in vitro cultures, the purified adenovirus in any of the forms described above is added to the culture medium for the infection of tumoral cells. To treat tumors in animal models or in human patients, the adenovirus can be administered locoregionally by injection in the tumor or in a body cavity where the tumor is located, or even systematically by injection into the bloodstream. As has been done with other adenovirus replications can be administered loco-regionally by injection in the tumor or in a body cavity where the tumor is located, or systemically by injection in the bloodstream. As has been done with other selective-replication adenoviruses, the treatment of tumors with the adenoviruses described that are the subject of this invention can be combined with other methods of treatment such as chemotherapy or radiotherapy.

EXAMPLES

Example 1

An oncolytic adenovirus with E1a regulated with the E2F1 promoter isolated with the DM sequence expresses E1a and is selectively replicated in tumor cells.

An adenovirus was constructed with E1a regulated with the E2F1 promoter isolated with the DM sequence as follows: To generate ICOVIR-1 (Ad-E2F-Δ24RGD), the human E2F1 promoter was obtained by PCR of mononuclear cells of human peripheral blood using oligonucleotides stretching from the pair of bases −218 to +51 of the E2F-1 promoter (position +1 indicates the start of transcription). The oligonucleotides contained KpnI and HindIII restriction targets for cloning in the plasmid pGL3 (Promega, Southampton, UK). The resulting plasmid was called pGL3-E2F. From this was obtained pE2F-Δ24 by recombination with a plasmid containing the 5,766 pairs of base from the extreme left of the adenoviral genome except nucleotides (nt) 122 and 129 of E1a (derived from pXC1-Δ24 with a HindIII site between nt 348 and nt 522 of the Ad5 genome[9]). pE2F-Δ24 was recombined with pShuttle[41] to obtain pShuttle-E2F-Δ24. This plasmid was linearized with PmeI and recombined with pVK503 (which contains the Ad5 sequence with the fiber modified with RDG[69]) to generate the plasmid pAd-E2F-Δ24RGD or pICOVIR-1. The combination of the E2F1 promoter and other modifications described in this invention with the E1a mutation called Δ24 and the insertion of the peptide RGD in the fiber was done to demonstrate that the modifications presented in this invention increases the oncolytic potency and selectivity of a virus known as selective towards Rb and powerful in the field of oncolysis (adenovirus Ad-Δ24RGD[70]). The mutation Δ24 and the insertion of peptide RGD are modifications described above in the field of virotherapy of cancer. In particular, they have been described together in reference 70 of this invention. This reference describes the use of the RGD peptide. This peptide is a tripeptide formed by the amino acids Arginine, Glycine and Aspartic Acid, which are bound to the integrins. Since the integrins are over-expressed in tumor cells, tripeptide RGD serves to increase the infectivity of the virus in tumor cells and is used for this purpose. The virus ICOVIR1 was generated by digestion with PacI of this plasmid and transfection in HEK293 cells. A parallel protocol was used to generate ICOVIR-2 (Ad-DM-E2F-Δ24RGD). The DM-1 insulating sequence was obtained from PCR of human peripheral mononuclear blood cells using oligonucleotides that amplify from nt 13006 to nt 13474 of locus DM1 (sequence published in GenBank with number L08835). This is represented by SEQ ID NO:8. Oligonucleotides of the PCR were designed to incorporate flanking sites Xho I. DM-1 was subcloned in XhoI of pShuttle-E2F-Δ24 described above to obtain pShuttle-DM-E2F-Δ24. The correct orientation of the DM1 fragment was verified by restriction with BamH1, Hindlll, XhoI and SmaI. pShuttle-DM-E2F-Δ24 is recombined with pVK503 to generate plCOVIR2. The virus ICOVIR2 was generated by digestion with PacI from this plasmid and transfection in HEK293 cells. ICOVIR1 and ICOVIR2 spread in the A549 line and were purified by methods described in gene therapy and virotherapy[36]. The correct structure of the genomes of ICOVIR-1 and ICOVIR-2 was verified by restriction with KpnI and HinIII, respectively. In addition, the DM-1 region, promoter E2F, mutation E1A-Δ24 and the region of the fiber containing RGD were sequenced. The oligonucleotides used for these sequencings are: DM1-Up (5'-GGGCAGATG-GAGGGCCTTTTATTC-3' □ (SEQ ID NO:4)), E2F-Up (5'-GTGTTACTCATAGCGCGTAA-3' (SEQ ID NO:5)), Δ24-down (5'-CCTCCGGTGATAATGACAAG-3' (SEQ ID NO:6)) and FiberUp (5'-CAAACGCTGTTGGATTTATG-3' (SEQ ID NO:7)). The sequences obtained are shown in SEQ. ID 1.

To demonstrate that an oncolytic adenovirus with E1a regulated with the E2F1 promoter isolated with the DM sequence expresses E1a selectively in tumor cells, we infected cell cultures of normal cells (murine and human hepatocytes, human fibroblasts and and human HUVEC endothelial cells) and tumoral (NP9 pancreas carcinoma cells) and tumor cells (cells of pancreas carcinoma NP9, lung carcinoma A549, head and neck carcinomata FaDu and SCC25, and melanoma SK-Mel-28 and 1.36.1.5) with ICOVIR1 and ICOVIR2 using multiple infections allowing more than 80% infection. After 20 hours post-infection, the cells were lysed in a lysis buffer (400 mM NaCl, 1 mM EDTA, 5 mM NaF, 10% glycerol, 1 mM sodium orthovanadate, 0.5% Nonidet P-40, 100 µg/ml phenylmethylsulfonyl fluoride, 1 µg/ml leupeptin and 10 µg/ml aprotinin in 10 mM Tris-HCl (pH 7.4) for 1 hour at 4° C. The lysate was centrifuged at 14,000 rpm, and the supernatant with proteins was separated by electrophoresis in 10% SDS-PAGE (25 µg/track, determined by Bradford, BioRad, CA, USA) and transferred to nitrocellulose (Schleicher and Schuell, Dassel, Germany). The membrane was blocked with 5% skimmed milk, 0.05% Tween 20 and 0.9% NaCl in 50 mM Tris (pH 7.5), and incubated for 16 hours at 4° C. with a polyclonal antibody anti-adenovirus-2-E1a (clone 13 S-5, Santa Cruz Biotechnology Inc., Santa Cruz, Calif., USA). E1a was detected with a secondary anti-rabbit IgG antibody (DAKO A/S) joined with peroxydase and Amersham's Enhanced Chemioluminescence protocol (Amersham, Arlington Heights, Ill., USA). The result is shown in FIG. 3 of this invention. It is shown that the presence of the E2F1 promoter (ICOVIR1) is capable of reducing the expression of E1a in normal cells. But the DM sequence confers greater control of the expression of E1a by the E2F promoter (ICOVIR2). In tumor cells, both ICOVIR1 and ICOVIR2 are capable of expressing E1a, but it is important to note that in some tumor lines such as FaDu, SCC25 and SKMel-28, the expression of E1a is less than that obtained with the salvage adenovirus and the oncolytic AdD24RGD in which E1a is not regulated by E2F1. This indicates that the E2F1 promoter, whether isolated or not with DM, does not have the necessary potency to enable a level of expression of E1a in tumor cells comparable to the salvage adenovirus.

To demonstrate that an oncolytic adenovirus with E1a regulated with the E2F1 promoter isolated with the DM sequence is replicated selectively in tumor cells, the cells were infected with ICOVIR1 and ICOVIR2 as described in the previous paragraph. Five days after infection, the cells and their culture media were collected and submitted to three cycles of freezing-thawing to release the virus. The quantity of the virus in the cell extract was determined by infection in HEK293 and anti-hexon staining using the monoclonal antibody 2Hx-2 (ATCC) and a secondary antibody, Alexa 488 anti-IgG of a rat (Molecular Probes, Eugene, Oreg.). The result is shown in FIG. 4. The presence of the E2F1 promoter in ICOVIR1 reduces viral replication in normal cells (fibroblasts and HUVEC). However, the isolating sequence in ICOVIR2 results in lower viral replication. In certain tumor-cell lines such as A549, ICOVIR1 and ICOVIR2 show a level of replication similar to the salvage adenovirus Adwt, but in the majority of tumor lines, its replicative capacity is less than that of Adwt.

Example 2

The Kozak sequence enables an increase in the expression of E1a an oncolytic adenovirus in which the expression of E1a is regulated with the E2F1 promoter isolated with the MD sequence.

An oncolytic adenovirus was constructed with E1a regulated with the E2F1 promoter isolated with the DM sequence and with the Kozak sequence to increase its translation. For this, a fragment of DNA containing the DM sequence, the E2F1 promoter and E1a was isolated from the pShuttle-MD-E2F-D24 described in example 1 by restriction with Kpn1 and subcloned in pGEM3Z (Promega), obtaining the plasmid pGEM-E2F-d24. This plasmid was used to replace the start of E1a translation using oligonucleotides with the Kozak sequence obtaining pGEM-E24-KD24. The Kpn1 fragment thus modified was recloned in Kpn1 from pShuttle-DM-E2F-D24 to obtain pShuttle-DM-E2F-KD24. Finally, pShuttle-DM-E2F-KD24 was recombined with pVK503 to obtain pICOVIR5. The virus ICOVIR5 was generated by digestion with PacI of this plasmid and transfection to HEK293 cells. ICOVIR5 was propagated in the A549 line and purified by methods described in gene therapy and virotherapy[36]. Its structure is presented in FIG. 1 of this invention. The correct sequence of the promoter and E1a was checked by restriction and sequencing. The sequence obtained is shown in SEQ. ID 2.

To demonstrate that E1a is expressed conditionally in tumor cells when its expression is regulated with the E2F1 promoter isolated with the DM sequence and in addition, its translation is optimized with the Kozak sequence, the expression of E1a was analyzed as described in example 1. In this case, it was included in oncolytic adenovirus ICOVIR5, which is distinguished from ICOVIR2 by the fact that it contains the Kozak sequence in the start of E1a translation. The results are shown in FIG. 5 of this invention. In normal cells ICOVIR5 does not express E1a by presenting the E2F promoter isolated with DM. In tumor cells, the level of expression of E1a is higher in ICOVIR5 than in ICOVIR2, which demonstrates the effect of the Kozak sequence to increase the potency of the promoter isolated with DM.

Example 3

The Kozak sequence enables an increase in the oncolytic potency of an adenovirus in which the expression of E1a is regulated with the E2F1 promoter isolated with the DM sequence.

We cultivated in cups of 96-cup plates cells from the tumor lines SKMel-28 and FaDu in which a reduction had been seen in the replicative capacity of ICOVIR2 (as described in example 1 and FIG. 4). These cells were infected with increasing quantities of ICOVIR5, ICOVIR2 and AdwtRGD (this last one used as a control for maximum lytic potency). Five days after infection, the quantity of protein was assessed by spectrophotometry as a reflection of cell survival. The results are shown in FIG. 6 of this invention. The lytic capacity of ICOVIR5 in SKMel-28 is the same as that of AdwtRGD and greater than that of ICOVIR2. In FaDu, it is also greater than ICOVIR2, although it does not reach the level of AdwtRGD.

Example 4

The modification of the E2F1 promoter by insertion of sites for bonding to E2F enables an increase in tumor cells of E1a expression when E1a is regulated by the E2F1 promoter isolated with the DM sequence and in addition, its translation is optimized with the Kozak sequence.

An oncolytic adenovirus was constructed with E1a regulated with an E2F1 promoter modified by the insertion of four sites for bonding to E2F. For this, in the plasmid pGEM-E2FKE1ad24 described in example 2, we introduced by directed mutagenesis a target for BsiWI in the E2F1 promoter (position 1326). In this site, BsiWI linked two copies of oligonucleotides with the palindromic sequence of bonding to E2F and that had extremes compatible with BsiWI. The promoter thus modified was subcloned in Kpn1 of pShuttle-MD-E2F-D24 to obtain pShMDE2FBsiE2F2KE1ad24. For homologous recombination of this plasmid with an AdwtRGD genome, the plasmid pICOVIR7 was obtained. The virus ICOVIR7 was generated by digestion in the A549 line and purified by methods described in gene therapy and virotherapy[36]. Its structure is presented in FIG. 1 of this invention. The correct sequence of the promoter and E1a was checked by restriction and sequencing. The sequence obtained is shown in SEQ. ID 3.

To demonstrate the role of the modified E2F1 promoter in the context of the isolation obtained with DM, we analyzed the expression of E1a in the tumor line 1.36.1.5 of melanoma by western blot as described in example 1. The oncolytic adenovirus ICOVIR7 is distinguished from ICOVIR5 by having the modified E2F1 promoter. The results are shown in FIG. 7 of this invention. The level of expression of E1a is greater in ICOVIR7, which demonstrates the potentiating role of the two additional sites for bonding to E2F in ICOVIR7. Furthermore, the addition of E1a is greater in ICOVIR5 than in ICOVIR2, which demonstrates once again the effect of the Kozak sequence in increasing the potency of the promoter isolated with DM.

Example 5

An adenovirus containing E1a regulated with the E2F1 promoter isolated with the DM sequence and the Kozak sequence at the start of E1a translation can be used to treat tumors effectively.

An experiment was performed in vivo with atymic rats from the Balb/c stock that contained NP9 tumors. A total of $1.2 \times 10^7$ tumor cells from the SKMel-28 line were injected subcutaneously in each rear side of the rat. After 15 days, the rats that had formed tumors (which reached 70-80 mm$^3$) were distributed in the different experimental groups (n=10 per group). The tumors of the control group received intratumoral injections of saline buffer (2×10 µl). Those of the group treated with icovir5 received intratumoral injections (2×10 µl) of icovir5 ($10^9$ viral particles per tumor). The tumors were measured each day and their volume estimated according to the formula: $V (mm^3) = A (mm) \times B^2 (mm^2) \times \pi/6$, where B is the transverse length. FIG. 8 shows the tumor volume compared with the start of treatment (day 0). The results are presented as a mean±SD. The existence of significant differences between results was calculated using a Mann-Whitney non-parametric study of data not paired. The growth curves were compared using a variance analysis. The results were considered significant if $p<0.05$. The calculations were made with the statistics package SPSS (SPSS Inc., Chicago, Ill.). There is a significant difference between tumor size on days 16 and 21.

In another experiment, treatment was performed by systemic injection of ICOVIR5. Tumors of the cell line of human melanoma SKMel-28 ($1.10^7$ cells/tumor) were planted in Balb C nu/nu atymic rats, and once established, were treated by administration in the tail vein with PBS, with a single injection on day 0 of ICOVIR-5 of $2.5.10^{10}$ viral particles (vp), or $1.10^{11}$ vp, or with an injection of $3.10^{10}$ vp and another of $1.10^{11}$ one hour apart. The results are shown in the lower part of FIG. 8 of this invention. All regimes of treatment with ICOVIR-5 showed oncolytic activity that results in a suppression of tumor growth that is significantly different from the control group (PBS), $p<0.05$. The administration of a pre-dose of $3.10^{10}$ vp before the injection of $1.10^{11}$ vp makes this regime significantly more effective than other models ($p<0.05$). The different sections of the tumors frozen in OCT were treated with an α-hexon antibody (a protein from the adenovirus capsid) and were counterstained with 4',6'-diaminidin-2-phenylindol. The anti-tumor activity of ICOVIR-5 corresponds to the replication of the adenovirus within the tumor, assessed in the tumors obtained on day 22 post-injection. The samples of all groups treated with ICOVIR-5 are positive for the presence of adenoviruses, which is located in areas of tumor necrosis.

Example 6

The toxicity associated with the systemic administration of adenoviruses is reduced when an adenovirus is used that contains E1a regulated with the E2F1 promoter isolated with the DM sequence and the Kozak sequence at the start of E1a translation.

The toxicity in vivo of an adenovirus that contains the Kozak sequence in E1a and an E2F1 promoter isolated by DM (ICOVIR5) was compared with that of a salvage virus and the oncolytic virus AdD24RGD that expresses E1a below the salvage promoter. The viruses were administered intravenously at different doses and at 5 days post-injection, we assessed parameters related to toxicity, such as animal survival, body weight, level of serum transaminases, and blood count. The results are shown in FIG. 9 of this invention. The lethal-dose 50 value ($LD_{50}$) for AdwtRGD or AdΔ24RGD in immunocompetent Balb/C rats is located in $5.10^{10}$ viral particles (vp)/rat on day 5 post-injection, while the double of this dose ($1.10^{11}$ vp/rat) is lethal for only 10% of rats ($LD_{10}$) injected with ICOVIR-5. The rats injected with $5.10^{10}$ vp of AdwtRGD or AdΔ24RGD on day 5 post-injection experienced significant weight loss, while the weight of the rats injected with ICOVIR-5 increased. In parallel, the measurements for liver transaminases in plasma on day 5 post-injection (mean values±SD; n=5-10/group) also revealed significant differences, with ICOVIR-5 being clearly less hepatotoxic at the same doses. The blood profile of the rats on day 5 showed that the administration of $5.10^{10}$ vp of ICOVIR-5 did not give rise to significant alterations in blood count, nor was there any reproduction of the significant thrombocytopenia associated with the administration of the same dose of AdwtRGD. The analysis of the expression of the adenoviral protein E1A in the rats' livers by immunodetection in frozen sections obtained on day 5 post-injection shows that the presence of an isolated version of the E2F-1 promoter in ICOVIR-5 is effective in restricting the expression of viral proteins, even when the dose administered is increased (FIG. 10). The histological assessment by staining with hematoxylin/eosin of sections in paraffin of the livers on day 3 post-injection also confirmed the low toxicity of ICOVIR-5 (FIG. 10). Thus, while the livers of rats that received $5.10^{10}$ vp of AdwtRGD or AdΔ24RGD presented clear symptoms of fulminant hepatitis (macrosteatosis, abundance of Councilman bodies and presence of points of necrosis), the animals injected with ICOVIR-5 had livers with a practically normal phenotype, which only marginally presented Councilman bodies in the most external regions.

REFERENCES

1 Alemany R, Balague C, Curiel D T. Replicative adenoviruses for cancer therapy. *Nat Biotechnot.* 2000; 18: 723-727.
2 De Pace N. Sulla scomparsa di un enorme cranco vegetante del collo dell'utero senza cura chirurgica. *Ginecogla.* 1912; 9: 82-89.
3 Sinkovics J, Horvath J. New developments in the virus therapy of cancer: a historical review. *Intervirology.* 1993; 36: 193-214.
4 Dupressoir T et al. Inhibition by parvovirus H-1 of the formation of tumors in nude mice and colonies in vitro by transformed human mammary epithelial cells. *Cancer Res.* 1989; 49: 3203-3208.
5 Stojdl D F et al. Exploiting tumor-specific defects in the interferon pathway with a previously unknown oncolytic virus. *Nat Med.* 2000; 6: 821-825.
6 Norman K L, Lee P W. Reovirus as a novel oncolytic agent. *J Clin Invest.* 2000; 105: 1035-1038.
7 Marked J M et al. Conditionally replicating herpes simplex virus mutant, G207 for the treatment of malignant glioma: results of a phase I trial. *Gene Ther.* 2000; 7: 867-874.
8 Shenk T. *Adenoviridae: The Viruses and Their Replication.* Lippincott-Raven Publishers: Philadelphia, 1996.
9 Fueyo J et al. A mutant oncolytic adenovirus targeting the Rb pathway produces anti-glioma effect in vivo. *Oncogene.* 2000; 19: 2-12.
10 Heise C et al. An adenovirus E1A mutant that demonstrates potent and selective systemic anti-tumoral efficacy. *Nat Med.* 2000; 6: 1134-1139.
11 Alemany R et al. Complementary adenoviral vectors for oncolysis. *Cancer Gene Ther.* 1999; 6: 21-25.
12 Hallenbeck P L et al. A novel tumor-specific replication-restricted adenoviral vector for gene therapy of hepatocellular carcinoma. *Hum Gene Ther.* 1999; 10: 1721-1733.
13 Rodriguez R et al. Prostate attenuated replication competent adenovirus (ARCA) CN706: a selective cytotoxic for prostate-specific antigen-positive prostate cancer cells. *Cancer Res.* 1997; 57: 2559-2563.
14 Kurihara T, Brough D E, Kovesdi I, Kufe D W. Selectivity of a replication-competent adenovirus for human breast carcinoma cells expressing the MUC1 antigen. *J Clin Invest.* 2000; 106: 763-771.
15 Matsubara S et al. A conditional replication-competent adenoviral vector, Ad-OC-E1a, to cotarget prostate cancer and bone stroma in an experimental model of androgen-independent prostate cancer bone metastasis. *Cancer Res.* 2001; 61: 6012-6019.
16 Ring C J, Harris J D, Hurst H C, Lemoine N R. Suicide gene expression induced in tumour cells transduced with recombinant adenoviral, retroviral and plasmid vectors containing the ERBB2 promoter. *Gene Ther.* 1996; 3: 1094-1103.
17 Shi Q, Wang Y, Worton R. Modulation of the specificity and activity of a cellular promoter in an adenoviral vector. *Hum Gene Ther.* 1997; 8: 403-410.
18 Brunori M, Malerba M, Kashiwazaki H, Iggo R. Replicating adenoviruses that target tumors with constitutive activation of the wnt signaling pathway. *J Virol.* 2001; 75: 2857-2865.
19 Doronin K et al. Tissue-specific, tumor-selective, replication-competent adenovirus vector for cancer gene therapy. *J Viral.* 2001; 75: 3314-3324.
20 Ryan P C et al. Antitumor efficacy and tumor-selective replication with a single intravenous injection of OAS403, an oncolytic adenovirus dependent on two prevalent alterations in human cancer. *Cancer Gene Thor.* 2004; 11: 555-569.
21 Johnson L et al. Selectively replicating adenoviruses targeting deregulated E2F activity are potent, systemic antitumor agents. *Cancer Cell.* 2002; 1: 325-337.
22 Working P K, Lin A, Borellini F. Meeting product development challenges in manufacturing clinical grade oncolytic adenoviruses. *Oncogene.* 2005; 24: 7792-7801.
23 Hearing P, Shenk T. The adenovirus type 5 E1A enhancer contains two functionally distinct domains: one is specific for E1A and the other modulates all early units in cis. *Cell.* 1986; 45: 229-236.
24 Buvoli M, Langer S J, Bialik S, Leinwand L A. Potential limitations of transcription terminators used as transgene insulators in adenoviral vectors. *Gene Ther.* 2002; 9: 227-231.
25 Yamamoto M et al. Transcription initiation activity of adenovirus left-end sequence in adenovirus vectors with e1 deleted. *J Virol.* 2003; 77: 1633-1637.
26 Steinwaerder D S, Lieber A. Insulation from viral transcriptional regulatory elements improves inducible transgene expression from adenovirus vectors in vitro and in vivo. *Gene Ther.* 2000; 7: 556-567.

27 Martin-Duque P, Jezzard S, Kaftansis L, Vassaux G. Direct comparison of the insulating properties of two genetic elements in an adenoviral vector containing two different expression cassettes. *Hum Gene Ther.* 2004; 15: 995-1002.

28 West A G, Gaszner M, Felsenfeld G. Insulators: many functions, many mechanisms. *Genes Dev.* 2002; 16: 271-288.

29 Tsukuda K et al. An E2F-responsive replication-selective adenovirus targeted to the defective cell cycle in cancer cells: potent antitumoral efficacy but no toxicity to normal cell. *Cancer Res.* 2002; 62: 3438-3447.

30 Jakubczak J L et al. An oncolytic adenovirus selective for retinoblastoma tumor suppressor protein pathway-defective tumors: dependence on E1A, the E2F-1 promoter, and viral replication for selectivity and efficacy. *Cancer Res.* 2003; 63: 1490-1499.

31 Dyson N. The regulation of E2F by pRB-family proteins. *Genes Dev.* 1998; 12: 2245-2262.

32 Filippova G N et al. CTCF-binding sites flank CTG/CAG repeats and form a methylation-sensitive insulator at the DM1 locus. *Nat Genet.* 2001; 28: 335-343.

33 O'Carroll S J et al. Quantifying adenoviral titers by spectrophotometry. Biotechniques. 2000; 28: 408-410, 412.

34 Neuman E, Flemington E K, Sellers W R, Kaelin W G, Jr. Transcription of the E2F-1 gene is rendered cell cycle dependent by E2F DNA-binding sites within its promoter. *Mol Cell Biol.* 1995; 15: 4660.

35 Kozak M. Point mutations define a sequence flanking the AUG initiator codon that modulates translation by eukaryotic ribosomes. *Cell.* 1986; 44: 283-292.

36 Graham F L, Prevec L. *Manipulation of adenoviral vectors*. Humana Press: Clifton, N.J., 1991.

37 Alemany R, Zhang W. *Oncolytic adenoviral vectors*. Humana Press: Totowa, N.J., 1999.

38 Davis A R et al. Construction of adenoviral vectors. *Mol Biotechnol.* 2001; 18: 63-70.

39 Mittereder N, March K L, Trapnell B C. Evaluation of the concentration and bioactivity of adenovirus vectors for gene therapy. *J Virol.* 1996; 70: 7498-7509.

40 Chartier C et al. Efficient generation of recombinant adenovirus vectors by homologous recombination in Escherichia coli. *J Vitol.* 1996; 70: 4805-4810.

41 He T C et al. A simplified system for generating recombinant adenoviruses. *Proc Natl Acad Sci USA.* 1998; 95: 2509-2514.

42 Kim D H, McCormick F. Replicating viruses as selective cancer therapeutics. *Mol Med Today.* 1996; 2: 519-527.

43 Kim D. Replication-selective oncolytic adenoviruses: virotherapy aimed at genetic targets in cancer. *Oncogene.* 2000; 19: 6660-6669.

44 Ring C J. Cytolytic viruses as potential anti-cancer agents. *J Gen Virol.* 2002; 83: 491-502.

45 Dobner T, Horikoshi N, Rubenwolf S, Shenk T. Blockage by adenovirus E4orf6 of transcriptional activation by the p53 tumor suppressor. *Science.* 1996; 272: 1470-1473.

46 Schaley J et al. Induction of the cellular E2F-1 promoter by the adenovirus E4-6/7 protein. *J Virol.* 2000; 74: 2084-2093.

47 Wickham T J. Targeting adenovirus. *Gene Ther.* 2000; 7: 110-114 the above report in.

48 Wickham T J et al. Increased in vitro and in vivo gene transfer by adenovirus vectors containing chimeric fiber proteins. *J Viral.* 1997; 71: 8221-8229.

49 Wickham T J, Roelvink P W, Brough D E, Kovesdi I. Adenovirus targeted to heparan-contalning receptors increases its gene delivery efficiency to multiple cell types. *Nat Biotechnol.* 1996; 14: 1570-1573.

50 Wickham T J, Carrion M E, Kovesdi I. Targeting of adenovirus penton base to new receptors through replacement of its RGD motif with other receptor-specific peptide motifs. *Gene Ther.* 1995; 2: 750-756.

51 Suzuki K et al. A conditionally replicative adenovirus with enhanced infectivity shows improved oncolytic potency. *Clin Cancer Res.* 2001; 7: 120-126.

52 Kasono K et al. Selective gene delivery to head and neck cancer cells via an integrin targeted adenoviral vector. *Clin Cancer Res.* 1999; 5: 2571-2579.

53 Hemminki A et al. Targeting oncolytic adenoviral agents to the epidermal growth factor pathway with a secretory fusion molecule. *Cancer Res.* 2001; 61: 6377-6381.

54 Gu D L et al. Fibroblast growth factor 2 retargeted adenovirus has redirected cellular tropism: evidence for reduced toxicity and enhanced antitumor activity in mice. *Cancer Res.* 1999; 59: 2608-2614.

55 Haisma H J et al. Targeting of adenoviral vectors through a bispecific single-chain antibody. *Cancer Gene Ther.* 2000; 7: 901-904.

56 Curiel D T. Strategies to adapt adenoviral vectors for targeted delivery. *Ann N Y Acad Sci.* 1999; 886: 158-171.

57 Croyle M A, Yu Q C, Wilson J M. Development of a rapid method for the PEGylation of adenoviruses with enhanced transduction and improved stability under harsh storage conditions. *Hum Gene Ther.* 2000; 11: 1713-1722.

58 Croyle M A, Chirmule N, Zhang Y, Wilson J M. "Stealth" adenoviruses blunt cell-mediated and humoral immune responses against the virus and allow for significant gene expression upon readministration in the lung. *J Virol.* 2001; 75: 4792-4801.

59 Alemany R, Suzuki K, Curiel D T. Blood clearance rates of adenovirus type 5 in mice. *J Gen Virol.* 2000; 81 Pt 11: 2605-2609.

60 O'Riordan C et al. PEGylation of adenovirus with retention of infectivity and protection from neutralizing antibody in vitro and in vivo. *Hum Gene Thor.* 1999; 10: 1349-1358.

61 Croyle M A, Cheng X, Wilson J M. Development of formulations that enhance physical stability of viral vectors for gene therapy. *Gene Ther.* 2001; 8: 1281-1290.

62 Croyle M A, Cheng X, Sandhu A, Wilson J M. Development of novel formulations that enhance adenoviral-mediated gene expression in the lung in vitro and in vivo. *Mol Ther.* 2001; 4: 22-28.

63 Ganly I et al. A phase I study of Onyx-015, an E1B attenuated adenovirus, administered intratumorally to patients with recurrent head and neck cancer. *Clin Cancer Res.* 2000; 6: 798-806.

64 Heise C et al. ONYX-015, an E1B gene-attenuated adenovirus, causes tumor-specific cytolysis and antitumoral efficacy that can be augmented by standard chemotherapeutic agents. *Nat Med.* 1997; 3: 639-645.

65 Heise C C, Williams A, Olesch J, Kim D H. Efficacy of a replication-competent adenovirus (ONYX-015) following intratumoral injection: intratumoral spread and distribution effects. *Cancer Gene Ther.* 1999; 6: 499-504.

66 Heise C C et al. Intravenous administration of ONYX-015, a selectively replicating adenovirus, induces antitumoral efficacy. *Cancer Res.* 1999; 59: 2623-2628.

67 Khuri F R et al. A controlled trial of intratumoral ONYX-015, a selectively-replicating adenovirus, in combination with cisplatin and 5-fluorouracil in patients with recurrent head and neck cancer. *Nat Med.* 2000; 6: 879-885.

68 Simons J, Henderson D. A phase I study of the intraprostatic injections of CN706, a prostate-specific antigen gene-regulated cytolytic adenovirus in patients with locally recurrent cancer following definitive radiotherapy. *Human Gene Therapy Protocol* 99802-236. National Institutes of Health. Recombinant DNA Advisory Committee. 1998.

68 Dmitriev I et al. An adenovirus vector with genetically modified fibers demonstrates expanded tropism via utilization of a coxsackievirus and adenovirus receptor-independent cell entry mechanism. *J Virol.* 1998; 72: 9706-9713.

69 Suzuki K et al. A conditionally replicative adenovirus with enhanced infectivity shows improved oncolytic potency. *Clin Cancer Res.* 2001; 7: 120-126.

What is claimed is:

1. An oncolytic adenovirus to treat cancer, the adenovirus comprising: an E1a gene, the E1a gene comprising a delta-24 mutation and operably linked to a tumor selective promoter that confers tumor selective expression of the E1a gene; and upstream of the promoter, a myotonic dystrophy insulator that comprises a CTCF binding site and insulates the promoter against transcriptional interference.

2. The oncolytic adenovirus according to claim 1, wherein a Kozak sequence is operably linked at the 5' end of the E1A gene to optimize protein translation.

3. The oncolytic adenovirus according to claim 1, wherein the adenovirus capsid is modified to increase infectivity or to direct the adenovirus to a receptor present on a tumor cell.

4. The oncolytic adenovirus according to claim 1, wherein a Kozak sequence is operably linked at the 5' end of the E1A gene to optimize protein translation; and the capsid is modified to increase infectivity or to direct the adenovirus to a receptor present on a tumor cell.

5. The oncolytic adenovirus according to claim 1, wherein the adenovirus further comprises one or more other genes encoding proteins chosen from prodrug activators, tumor suppressors, and immunostimulators.

6. The oncolytic adenovirus according to claim 1, wherein a Kozak sequence is operably linked at the 5' end of the E1A gene to optimize protein translation; and the adenovirus comprises one or more other genes encoding proteins chosen from prodrug activators, tumor suppressors, and immunostimulators.

7. The oncolytic adenovirus according to claim 1, wherein the adenovirus is a human adenovirus serotype from 1 to 50.

8. The oncolytic adenovirus according to claim 7, wherein the adenovirus genome is from a human adenovirus serotype 5.

9. The oncolytic adenovirus according to claim 1, wherein the promoter is the promoter of human gene E2F1.

10. The oncolytic adenovirus according to claim 9, wherein the E2F1 promoter is modified by the insertion of additional binding sites to E2F.

11. A pharmaceutical composition comprising an effective amount of the oncolytic adenovirus according to claim 1, and one or more components chosen from carriers and pharmaceutically acceptable excipients.

12. The oncolytic adenovirus according to claim 1, wherein the sequence of the insulator comprises position 368 to 1096 of the nucleotide sequence of SEQ ID No:1.

\* \* \* \* \*

SEQUENCE LISTING

```
<160> NUMBER OF SEQ ID NOS: 8

<210> SEQ ID NO 1
<211> LENGTH: 1641
<212> TYPE: DNA
<213> ORGANISM: Artificial Sequence
<220> FEATURE:
<223> OTHER INFORMATION: Description of Artificial Sequence: Synthetic
      recombinant adenovirus polynucleotide

<400> SEQUENCE: 1
catcatcaat tataccttcc attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tctctagcat cgatgtcgag     360
ggatccctcg agaccctgaa actgtcttcg actccggggc cccgttggaa gactgagtgc     420
ccggggcacg gcacagaagc cgcgcccacc gcctgccagt tcacaaccgc tccgagcgtg     480
ggtctccgcc cagctccagt cctgtgatcc gggcccgccc cctagcggcc ggggagggag     540
gggccgggtc cgcggccggc gaacggggct cgaagggtcc ttgtagccgg gaatgctgct     600
gctgctgctg gggggatcac agaccatttc tttctttcgg ccaggctgag gccctgacgt     660
ggatgggcaa actgcaggcc tgggaaggca gcaagccggg ccgtccgtgt tccatcctcc     720
acgcaccccc acctatcgtt ggttcgcaaa gtgcaaagct ttcttgtgca tgacgccctg     780
ctctggggag cgtctggcgc gatctctgcc tgcttactcg ggaaatttgc ttttgccaaa     840
cccgcttttt cggggatccc gcgccccct cctcacttgc gctgctctcg gagcccagc      900 cggctccgcc cgcttcggcg gtttggatat ttattgacct cgtcctccga ctcgctgaca     960
ggctacagga cccccaacaa ccccaatcca cgttttggat gcactgagac cccgacattc    1020
ctcggtattt attgtctgtc cccacctagg accccacc ccgaccctcg cgaataaaag      1080
gccctccatc tgcccctcga gtctagagat ggccgcaata aaatatcttt attttcatta    1140
catctgtgtg ttggtttttt gtgtgaatcg atagtactaa catacgctct ccatcaaaac    1200
aaaacgaaac aaaacaaact agcaaaatag gctgtcccca gtgcaagtgc aggtgccaga    1260
acatttctct atcgataggt accatccgga caaagcctgc gcgcgccccg ccccgccatt    1320
ggccgtaccg ccccgcgccg ccgccccatc tcgccctcg ccgccgggtc cggcgcgtta     1380
aagccaatag gaaccgccgc cgttgttccc gtcacggccg gggcagccaa ttgtggcggc    1440
gctcggcggc tcgtggctct ttcgcggcaa aaaggatttg gcgcgtaaaa gtggccggga    1500
ctttgcaggc agcggcggcc gggggcggag cgggatcgag ccctcgccga ggcctgccgc    1560
catgtcgaga tctaagtaag ctatcgaatt caagcttgtt ttctcctccg agccgctccg    1620
```
acaccgggac tgaaaatgag a                                              1641

<210> SEQ ID NO 2
<211> LENGTH: 1556
<212> TYPE: DNA
<213> ORGANISM: Artificial Sequence
<220> FEATURE:
<223> OTHER INFORMATION: Description of Artificial Sequence: Synthetic
      recombinant adenovirus polynucleotide

<400> SEQUENCE: 2

| | | |
|---|---|---|
| catcatcaat tataccttcc attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgtttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tctctagcat cgatgtcgag | 360 |
| gatccctcga gaccctgaaa ctgtcttcga ctccggggcc ccgttggaag actgagtgcc | 420 |
| cggggcacgg cacagaagcc gcgcccaccg cctgccagtt cacaaccgct ccgagcgtgg | 480 |
| gtctccgccc agctccagtc ctgtgatccg ggcccgcccc ctagcggccg gggagggagg | 540 |
| ggccgggtcc gcggccggcg aacggggctc gaagggtcct tgtagccggg aatgctgctg | 600 |
| ctgctgctgg ggggatcaca gaccatttct ttctttcggc caggctgagg ccctgacgtg | 660 |
| gatgggcaaa ctgcaggcct gggaaggcag caagccgggc cgtccgtgtt ccatcctcca | 720 |
| cgcacccca cctatcgttg gttcgcaaag tgcaaagctt tcttgtgcat gacgccctgc | 780 |
| tctggggagc gtctggcgcg atctctgcct gcttactcgg gaaatttgct tttgccaaac | 840 |
| ccgcttttc ggggatcccg cgccccctc ctcacttgcg ctgctctcgg agccccagcc | 900 |
| ggctccgccc gcttcggcgg tttggatatt tattgacctc gtcctccgac tcgctgacag | 960 |
| gctacaggac ccccaacaac cccaatccac gttttggatg cactgagacc ccgacattcc | 1020 |
| tcggtattta ttgtctgtcc ccacctagga ccccaccc cgaccctcgc gaataaaagg | 1080 |
| ccctccatct gcccctcgag tctagagatg ccgcaataa aatatcttta ttttcattac | 1140 |
| atctgtgtgt tggttttttg tgtgaatcga tagtactaac atacgctctc catcaaaaca | 1200 |
| aaacgaaaca aaacaaacta gcaaatagg ctgtccccag tgcaagtgca ggtgccagaa | 1260 |
| catttctcta tcgataggta ccatccggac aaagcctgcg cgcgccccgc ccgccattg | 1320 |
| gccgtaccgc cccgcgccgc cgccccatct cgccctcgc gccgggtcc ggcgcgttaa | 1380 |
| agccaatagg aaccgccgcc gttgttcccg tcacggccgg ggcagccaat tgtggcggcg | 1440 |
| ctcggcggct cgtggctctt tcgcggcaaa aaggatttgg cgcgtaaaag tggccgggac | 1500 |
| tttgcaggca gcggcggccg ggggcggagc gggatcgagc cctcgccacc atgaga | 1556 |

<210> SEQ ID NO 3
<211> LENGTH: 1680
<212> TYPE: DNA
<213> ORGANISM: Artificial Sequence
<220> FEATURE:
<223> OTHER INFORMATION: Description of Artificial Sequence: Synthetic
      recombinant adenovirus polynucleotide

<400> SEQUENCE: 3

| | | |
|---|---|---|
| catcatcaat tataccttcc attttggatt gaagccaata tgataatgag ggggtggagt | 60 |
| ttgtgacgtg gcgcggggcg tgggaacggg gcgggtgacg tagtagtgtg gcggaagtgt | 120 |

```
gatgttgcaa gtgtggcgga acacatgtaa gcgacggatg tggcaaaagt gacgttttttg      180 gtgtgcgccg tgtacacag gaagtgacaa ttttcgcgcg gttttaggcg gatgttgtag        240
taaatttggg cgtaaccgag taagatttgg ccattttcgc gggaaaactg aataagagga       300
agtgaaatct gaataatttt gtgttactca tagcgcgtaa tctctagcat cgatgtcgag       360
gatccctcga gaccctgaaa ctgtcttcga ctccggggcc ccgttggaag actgagtgcc       420
cggggcacgg cacagaagcc gcgcccaccg cctgccagtt cacaaccgct ccgagcgtgg       480
gtctccgccc agctccagtc ctgtgatccg ggcccgcccc ctagcggccg gggagggagg       540
ggccgggtcc gcggccggcg aacgggctc gaagggtcct tgtagccggg aatgctgctg        600
ctgctgctgg ggggatcaca gaccatttct ttctttcggc caggctgagg ccctgacgtg       660
gatgggcaaa ctgcaggcct gggaaggcag caagccgggc cgtccgtgtt ccatcctcca       720 cgcacccca cctatcgttg gttcgcaaag tgcaaagctt tcttgtgcat gacgccctgc         780
tctggggagc gtctggcgcg atctctgcct gcttactcgg gaaatttgct tttgccaaac       840
ccgctttttc ggggatcccg cgcccccctc ctcacttgcg ctgctctcgg agcccagcc        900 ggctccgccc gcttcggcgg tttggatatt tattgacctc gtcctccgac tcgctgacag      960
gctacaggac ccccaacaac cccaatccac gttttggatg cactgagacc ccgacattcc      1020
tcggtattta ttgtctgtcc ccacctagga cccccacccc cgaccctcgc gaataaaagg      1080
ccctccatct gcccctcgag tctagagatg ccgcaataa aatatcttta ttttcattac       1140
atctgtgtgt tggttttttg tgtgaatcga tagtactaac atacgctctc catcaaaaca      1200
aaacgaaaca aaacaaacta gcaaaatagg ctgtccccag tgcaagtgca ggtgccagaa      1260
catttctcta tcgataggta ccatccggac aaagcctgcg cgcgcccgc cccgccattg        1320 gcgtacgtcg gcggctcgtg gctctttcgc ggcaaaaagg atttggcgcg taaaagtggt      1380
tcgaagtact cggcggctcg tggctctttc gcggcaaaaa ggatttggcg cgtaaaagtg      1440
gttcgaagta ccgccccgcg ccgccgcccc atctcgcccc tcgccgccgg gtccggcgcg      1500
ttaaagccaa taggaaccgc cgccgttgtt cccgtcacgg ccggggcagc caattgtggc      1560
ggcgctcggc ggctcgtggc tctttcgcgg caaaaaggat ttggcgcgta aaagtggccg      1620
ggactttgca ggcagcggcg gccggggcg gagcgggatc gagccctcgc caccatgaga       1680
```

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide DM1-Up

<400> SEQUENCE: 4
gggcagatgg agggccttt attc                                               24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide E2F-Up

<400> SEQUENCE: 5
gtgttactca tagcgcggta a                                                 21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide delta24-Down

<400> SEQUENCE: 6
cctccggtgg ataatgacaa g                                              21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide FiberUp

<400> SEQUENCE: 7
caaacgctgt tggatttatg                                                20

<210> SEQ ID NO 8
<211> LENGTH: 469
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotides 13006 to 13474 of locus DM1
      (sequence published in GenBank with number L08835)

<400> SEQUENCE: 8
aaccctagaa ctgtcttcga ctccggggcc ccgttggaag actgagtgcc cggggcacgg      60
cacagaagcc gcgcccaccg cctgccagtt cacaaccgct ccgagcgtgg gtctccgccc     120
agctccagtc ctgtgtaccg ggcccgcccc ctagcggccg gggagggagg ggccgggtcc     180
gcggccggcg aacggggctc gaagggtcct tgtagccggg aatgctgctg ctgctgctgc     240
tgctgctgct gctgctgggg ggatcacaga ccatttcttt ctttcggcca ggctgaggcc     300
ctgacgtgga tgggcaaact gcaggcctgg gaaggcagca gccgggccg tccgtgttcc      360 atcctccacg cacccccacc tatcgttggt tcgcaaagtg caaagctttc ttgtgcatga     420
cgccctgctc tggggagcgt ctggcgcgat ctctgcctgc ttactcggg                469